(12) United States Patent
Nishizaki

(10) Patent No.: US 9,729,982 B2
(45) Date of Patent: Aug. 8, 2017

(54) HEARING AID FITTING DEVICE, HEARING AID, AND HEARING AID FITTING METHOD

(71) Applicant: Panasonic Intellectual Property Management Co., Ltd., Osaka (JP)

(72) Inventor: Makoto Nishizaki, Fukuoka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 58 days.

(21) Appl. No.: 14/404,757

(22) PCT Filed: Jun. 6, 2013

(86) PCT No.: PCT/JP2013/003591
§ 371 (c)(1),
(2) Date: Dec. 1, 2014

(87) PCT Pub. No.: WO2013/190791
PCT Pub. Date: Dec. 27, 2013

(65) Prior Publication Data
US 2015/0146876 A1    May 28, 2015

(30) Foreign Application Priority Data
Jun. 19, 2012  (JP) ................. 2012-137513

(51) Int. Cl.
*H04R 29/00* (2006.01)
*H04R 25/00* (2006.01)
*A61B 5/12* (2006.01)

(52) U.S. Cl.
CPC .............. *H04R 25/70* (2013.01); *A61B 5/123* (2013.01)

(58) Field of Classification Search
CPC ................................ H04R 25/70; A61B 5/123
See application file for complete search history.

(56) References Cited

U.S. PATENT DOCUMENTS 8,548,179 B2    10/2013  Nishizaki
2009/0279726 A1  11/2009  Baskent
(Continued)

FOREIGN PATENT DOCUMENTS

JP    8-317495    11/1996
JP    2000-125396    4/2000
(Continued)

OTHER PUBLICATIONS

International Search Report issued Sep. 3, 2013 in International (PCT) Application No. PCT/JP2013/003591.

*Primary Examiner* — Andrew L Sniezek
(74) *Attorney, Agent, or Firm* — Wenderoth, Lind & Ponack, L.L.P.

(57) ABSTRACT

The present invention relates to a hearing aid fitting device, and an objective thereof is to improve usability thereof. To achieve this object, the fitting device (1) of the present invention comprises a hierarchical classification database (12) and an adjustment data determination component (20). A plurality of pieces of adjustment difference data obtained by the fitting of a hearing aid is hierarchically classified according to similarity in the amount of adjustment and is saved in the hierarchical classification database (12). The adjustment data determination component (20) determines fine adjustment data for the hearing aid by selecting a cluster from among a plurality of clusters in each hierarchical layer.

20 Claims, 19 Drawing Sheets

(56) References Cited

U.S. PATENT DOCUMENTS

| | | |
|---|---|---|
| 2010/0234757 A1 | 9/2010 | Stromsted |
| 2012/0070023 A1 | 3/2012 | Nishizaki |
| 2013/0202123 A1* | 8/2013 | Nishizaki ............... H04R 25/70 381/60 |

FOREIGN PATENT DOCUMENTS

| | | |
|---|---|---|
| JP | 2001-175637 | 6/2001 |
| JP | 2003-501986 | 1/2003 |
| JP | 2011-504691 | 2/2011 |
| WO | 00/78096 | 12/2000 |
| WO | 2011/132403 | 10/2011 |

* cited by examiner

| | 1 | 2 | 3 | 4 | 5 | 6 | 7 | 8 | | N |
|---|---|---|---|---|---|---|---|---|---|---|
| N | | | | | | | | | | - |
| | | | | | | | | | | |
| 8 | | | | | | | | - | | 36 |
| 7 | | | | | | | - | 15 | | 21 |
| 6 | | | | | | - | 27 | 20 | | 24 |
| 5 | | | | | - | 39 | 12 | 25 | | 27 |
| 4 | | | | - | 9 | 34 | 15 | 20 | | 34 |
| 3 | | | - | 14 | 19 | 20 | 7 | 8 | | 28 |
| 2 | | - | 9 | 5 | 14 | 29 | 16 | 15 | | 35 |
| 1 | - | (15) | 8 | 20 | 25 | 14 | 15 | 16 | | 20 |
| | 1 | 2 | 3 | 4 | 5 | 6 | 7 | 8 | | N |

HEARING AID FITTING DEVICE, HEARING AID, AND HEARING AID FITTING METHOD

TECHNICAL FIELD

The present invention relates to a hearing aid fitting device, a hearing aid, and a hearing aid fitting method with which fitting parameters suited to the hearing ability of a patient can be easily set.

BACKGROUND ART

A hearing aid fitting device that is used to make usage settings for a hearing aid sets (fits) the hearing aid characteristics of the hearing aid to match the hearing ability of the user of that hearing aid. To this end, first the hearing ability of the user is measured from low- to high-pitched sounds in the audible frequency band. Next, the hearing aid characteristics are adjusted based on this hearing ability data. However, this processing often takes a long time, even for an experienced adjustment technician.

Specifically, the sense of hearing varies greatly from one person to the next, and also depends on the measurement environment (the season of the year, the size of the measurement space, etc.), the time of day, the person's physical condition, and so forth. Therefore, these are all factors that can make the adjustment take longer. More specifically, even though the goal is to adjust the hearing aid so that the final settings are gradually reached, it is common for the user to say that the last sound was better, causing the adjustment technician to have to go back. As a result, the adjustment ends up taking a long time. In view of this, there have been studies into ways to set these hearing aid characteristics in less time by utilizing an interactive genetic algorithm (see Patent Literature 1 below, for example). Using this interactive genetic algorithm allows the fitting to be performed merely by having the user listen to and compare a number of parameters supplied from the system.

CITATION LIST

Patent Literature

Patent Literature 1: Japanese Laid-Open Patent Application 2001-175637

SUMMARY

Technical Problem

Nevertheless, before an adjustment result that satisfies the user can actually be obtained, it is necessary to repeatedly carry out a process in which recombination, mutation, and other such operations are performed on the basis of the above-mentioned listening and comparing, and listening and comparing are again performed for the parameters obtained as a result of this. Specifically, if ten parameters are adjusted after listening and comparing one time, the subsequent recombination or mutation operation must be repeated ten times, for example, until the listening and comparing results converge.

Thus, when an interactive genetic algorithm is utilized, the user can perform adjustment himself, but the job ends up taking a very long time.

In view of this, and with the above-mentioned problems encountered with a conventional hearing aid fitting device in mind, it is an object of the present invention to provide a hearing aid fitting device, a hearing aid, a hearing aid fitting method, a program, and a recording medium with which fitting entails less work and can be carried out more efficiently and in less time.

Solution to Problem

To achieve this object, the hearing aid fitting device of the first invention comprises a database and an adjustment data determination component. The database is such that a plurality of sets of previously acquired adjustment data obtained by the fitting of a hearing aid are stored after being hierarchically classified according to the similarity in the amount of adjustment. The adjustment data determination component determines adjustment data for the hearing aid by selecting a classification from among a plurality of classifications in each hierarchical layer.

The hearing aid of the second invention comprises a receiver, an adjustment data determination component, a hearing aid processor, and an output component. The receiver receives audio. The adjustment data determination component is connected to a database in which previously acquired adjustment data obtained by the fitting of a hearing aid is stored after being hierarchically classified according to the similarity in the amount of adjustment, and determines adjustment data for the hearing aid by selecting a classification from among a plurality of classifications in each hierarchical layer. The hearing aid processor performs hearing aid processing on the received audio, on the basis of the adjustment data thus determined. The output component outputs the audio that has undergone hearing aid processing.

The hearing aid of the third invention comprises a receiver, an adjustment data determination component, a hearing aid processor, and an output component. The receiver receives audio. The adjustment data determination component is connected to a database in which a plurality of sets of previously acquired adjustment data obtained by the fitting of a hearing aid are stored so as to be capable of rearrangement on the basis of a specific priority order, and determines adjustment data for the hearing aid by selecting one set of previously acquired adjustment data from among a plurality of sets of rearranged previously acquired adjustment data. The hearing aid processor performs hearing aid processing on the received audio, on the basis of the adjustment data thus determined. The output component outputs the audio that has undergone hearing aid processing.

Advantageous Effects

The present invention provides a hearing aid fitting device, a hearing aid, a hearing aid fitting method, a program, and a recording medium with which fitting entails less work and can be carried out more efficiently and in less time.

BRIEF DESCRIPTION OF DRAWINGS

FIG. 16 is a diagram illustrating the hearing aid fitting method in Embodiment 3 of the present invention;

DESCRIPTION OF EMBODIMENTS

The fitting device in an embodiment pertaining to the present invention will now be described through reference to the drawings.

Shortening Time Required for Adjustment

First, how the time it takes for adjustment work is shortened, which is the object of this embodiment, will be briefly described.

In the fitting of a hearing aid, first the hearing ability of the user is measured from low- to high-pitched sounds in the audible frequency band. Then, based on this hearing ability data, an initial fitting is performed using an initial adjustment method such as a fitting theory, and the values of various fitting parameters are found as initial adjustment data. Fine adjustment is then performed on the initial adjustment data, and the final adjustment data that will ultimately be used for the hearing aid is found.

In this hearing aid fitting, the inventors analyzed samples of adjustment difference data for about 200 patients. The adjustment difference data (an example of previously acquired adjustment data) here is data related to the final adjustment data for other patients that have undergone fitting in the past, and is a change amount indicating how much various fitting parameter values have been changed by fine adjustment from the initial adjustment data found by the initial adjustment method, such as NAL-NL1. This is also called fine adjustment data.

The inventors analyzed this change amount, and consequently learned that typical parameters of fine adjustment performed by a fitter to suit the user of the hearing aid can be extracted as a classification parameter by classifying the above-mentioned change amount according to similarity. In view of this, the inventors came up with the idea of efficiently performing fitting by utilizing this classified adjustment difference data.

The hearing aid fitting device in Embodiment 1 pertaining to the present invention will now be described.

Embodiment 1

Overview of Configuration of Fitting Device 1

Figure 1:
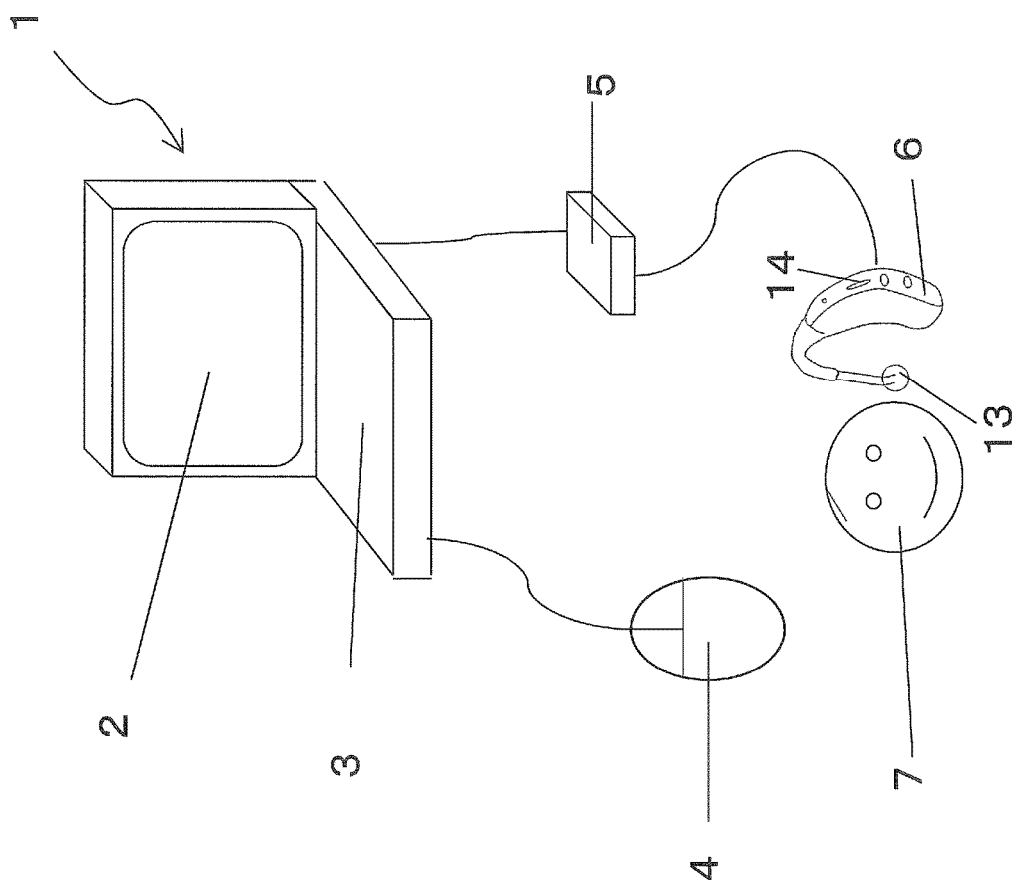
FIG. 1 is a configuration diagram of a hearing aid fitting device in Embodiment 1 of the present invention.
Figure 2:
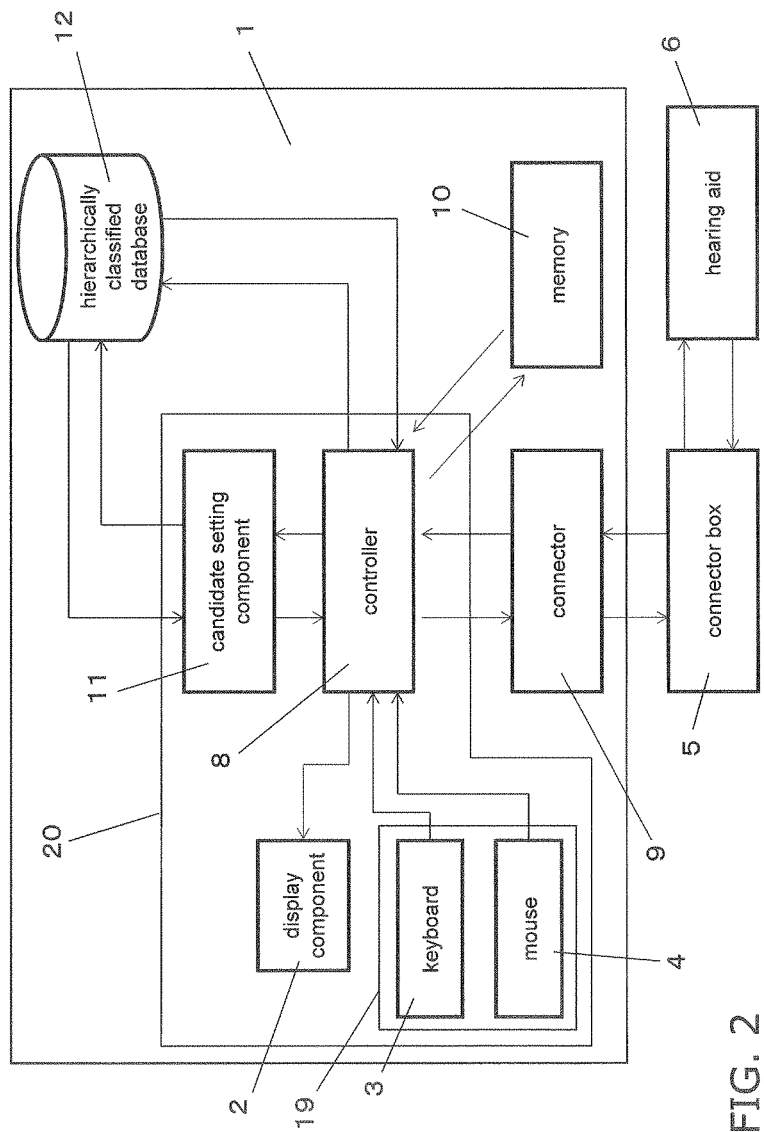
FIG. 2 is a control block diagram of the hearing aid fitting device shown in FIG. 1.

FIG. 1 is a diagram of the configuration of the fitting device 1 in Embodiment 1. As shown in FIG. 1, the hearing aid fitting device 1 in this embodiment (an example of a hearing aid fitting device) adjusts hearing aid parameters matched to a patient, with the configuration in FIG. 1. FIG. 2 is a control block diagram of the fitting device in this embodiment. The fitting device 1 comprises a hierarchically classified database 12 and an adjustment data determination component 20.

The adjustment data determination component 20 determines the various values of fitting parameters. The adjustment data determination component 20 comprises a display component 2 that displays various information during fitting, and a keyboard 3 and a mouse 4 as input components for inputting information to the fitting device 1. Although discussed in greater detail below, the keyboard 3 and the mouse 4 also function as a selector 19 in the selection of classifications. The fitting device 1 is connected to a hearing aid 6 via a connector box 5, and this hearing aid 6 is worn in the ear of a user 7 (patient). This hearing aid 6 has an earphone 13 that emits sound toward the ear hole of the user 7, and a microphone 14 that is disposed facing away from the user 7 in a state in which the hearing aid 6 is worn on the ear, and that receives sound from the outside.

The user 7 operates the keyboard 3, the mouse 4, etc., according to an instruction or question about fitting displayed on the display component 2. The user 7 then sets a fitting parameter corresponding to the result of this operation in the hearing aid 6 via the connector box 5, and an evaluation sound reflecting this fitting parameter is outputted from the earphone 13 of the hearing aid 6.

The user 7 then continues to adjust the hearing aid 6 to his liking while listening to the evaluation sounds actually outputted from the hearing aid 6. In this embodiment, the patient and the person operating the fitting device 1 are both the same person, that is, the user 7, but in actual practice the person operating the fitting device 1 may be a fitting specialist, a salesperson of a retail store, or the like.

Also, the evaluation was outputted from the hearing aid 6 above, but the configuration may be such that a speaker may be installed in the fitting device 1, a fitting parameter is written to the hearing aid 6, and then a test sound is outputted from the speaker, so that the user test-listens to evaluation sounds obtained by subjecting sounds brought in from the microphone 14 of the hearing aid to hearing aid processing.

Control Configuration of Fitting Device 1

FIG. 2 is a control block diagram of the fitting device 1. As shown in FIG. 2, the fitting device 1 comprises a controller 8 that performs various kinds of computation. This controller 8 is connected to the display component 2 that displays various kinds of information during fitting work, and to the keyboard 3 and mouse 4 used to input various kinds of information. The controller 8 is also connected to the connector box 5 and the hearing aid 6 via a connector 9 that can be unplugged.

The controller 8 is also connected to a memory 10 and to the hierarchically classified database 12 via a candidate setting component 11. This memory 10 temporarily stores software for performing the fitting of this embodiment, the operation results from the computation process, and so forth.

The candidate setting component 11 identifies a fitting data candidate presented on the display unit 2 in a user operation (discussed below). The hierarchically classified database 12 hierarchically stores adjustment difference data.

When we say that the candidate setting component 11 identifies fitting data, it means that the necessary adjustment difference data is read out from the adjustment difference data stored in the hierarchically classified database 12.

Hierarchically Classified Database 12

Figure 3:
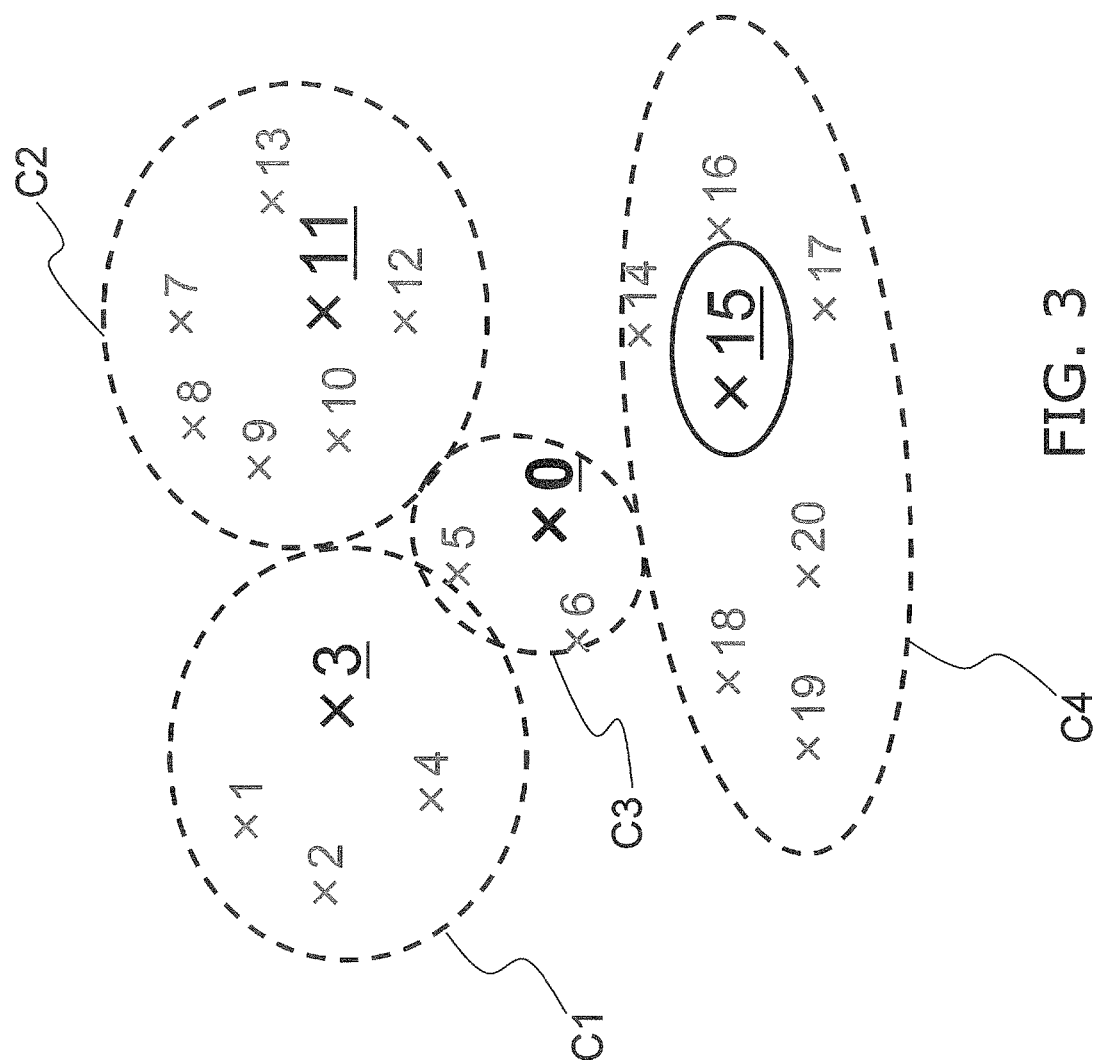
FIG. 3 is a diagram illustrating a hearing aid fitting method in Embodiment 1 of the present invention.

FIG. 3 is a diagram in which the adjustment difference data stored in the hierarchically classified database 12 has been classified according the similarity of this adjustment difference data and represented as a two-dimensional adjustment difference data map. The actual number of samples is about 200, but only 20 samples will be described in this example in order to simplify the description. X1 to X20 indicate these samples.

First, the adjustment difference data disposed on the two-dimensional map is classified into four patterns (an example of classification), from cluster C1 to cluster C4, according to the degree of similarity. In this example, the four people of X1 to X4 are classified as cluster C1, the six people of X7 to X12 are classified as cluster C2, the two people of X5 and X6 are classified as cluster C3, and the seven people of X14 to X20 are classified as cluster C4. The data was classified into four patterns here, but it may instead be classified into two patterns, six patterns, eight patterns, or the like. The number of patterns to be classified corresponds to the number of selection branches (discussed below), and therefore should be a number that affords good readability.

X0 expresses the initial adjustment data, which is a parameter of initial adjustment that has not yet undergone fine adjustment, and shows the initial state determined from the hearing ability of the user 7 and a fitting theory. The fitting theory here can be the above-mentioned NAL-NL1 (National Acoustic Laboratories-non-linear 1), NAL-NL2, DSL (desired sensation level), i/o, DSLv5, POGO (prescription of gain/output), FIG. 6, etc. Examples of fitting parameters include gain, compression, and TK (threshold knee point), and these are provided, for example, at frequencies of 250, 500, 1 k, 2 k, and 4 k hertz (Hz), etc.

In clusters C1 to C4, the part closest to the middle of each cluster is set as the representative characteristics of that cluster. For instance, the average value of the fine adjustment parameter at each frequency included in each cluster (an example of classification) may be used as the centroid, and the parameter closest to this centroid may be used as a representative characteristic. Samples that are in bold and underlined in FIG. 3 are representative characteristics, which are X3 in cluster C1, X11 in cluster C2, X0 in cluster C3, and X15 in cluster C4. The user 7 listens to and compares these representative characteristics. That is, the user listens to and compares sounds adjusted with the adjustment data of these representative characteristics (centroid adjustment data).

Figure 6:
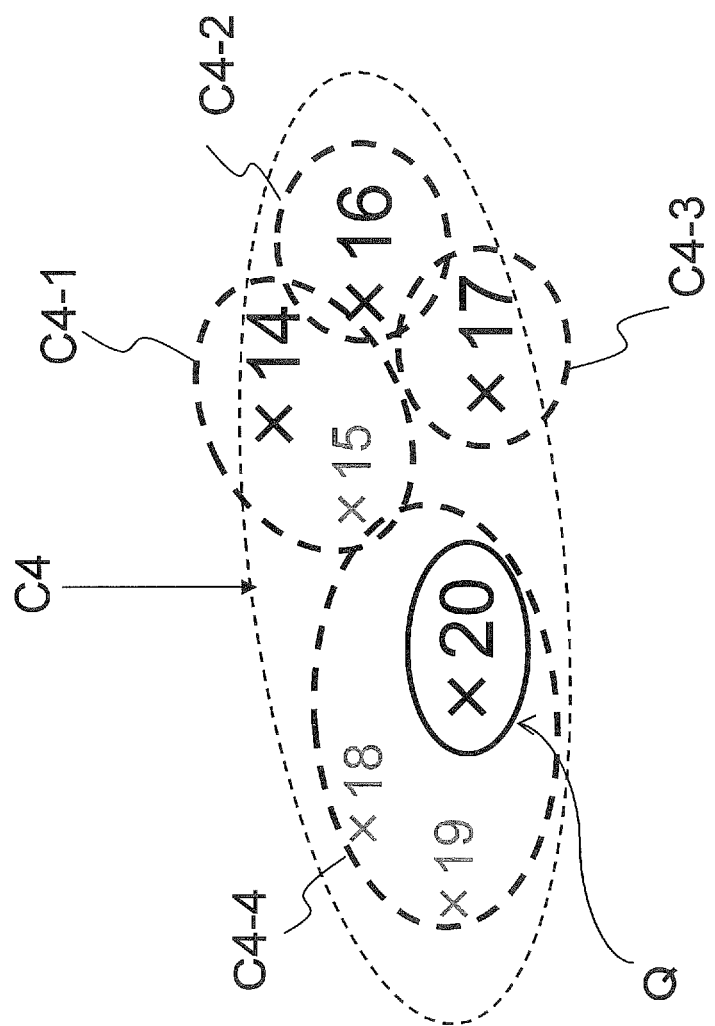
FIG. 6 is a diagram illustrating the hearing aid fitting method in Embodiment 1 of the present invention.

At the first hierarchical level shown in FIG. 3, the hierarchically classified database 12 is classified into the four clusters C1 to C4, but may be classified into other hierarchical levels. Specifically, as shown in FIG. 6 (discussed below), the cluster C4 is further classified into four clusters C4-1 to C4-4. Any known method (such as the nearest neighbor method, the furthest neighbor method, category-average method, centroid method, median method, or Ward method) can be used as the method for hierarchically performing this cluster classification. For example, the fitting parameters for the samples X1 to X20 can be put in a vector display, and the distance between these vectors calculated, with the conclusion being that the shorter is the distance, the greater is the similarity between the fitting parameters. All of the fitting parameters may be used as parameters for calculating similarity, or just some of the parameters may be used.

For example, for values of a sample Xm (gain, compression, TK, etc.) of n number of fitting parameters of initial adjustment data obtained by initial fitting by a fitting theory, if a vector component display is used and represented as $(Xm1, Xm2, Xm3, \ldots, Xmn)$, and the amount of change in the fitting parameters from the initial fitting due to fine adjustment is represented as $(\delta m1, \delta m2, \delta m3, \ldots, \delta mn)$, then the individual values for the fitting parameters of the final adjustment data for the sample Xm is represented as $(Xm1+\delta m1, Xm2+\delta m2, Xm3+\delta m3, \ldots, Xmn+\delta mn)$. The above-mentioned adjustment difference data refers to $(\delta m1, \delta m2, \delta m3, \ldots, \delta mn)$, and is also called fine adjustment fitting parameters. The above-mentioned X0 is when the values for the fine adjustment fitting parameters are all zero.

Because of the above, the adjustment difference data for the sample X1 is represented as $(\delta 11, \delta 12, \delta 13, \ldots, \delta 1n)$, and the adjustment difference data for the sample X2 is represented as $(\delta 21, \delta 22, \delta 23, \ldots, \delta 2n)$. The inter-vector distance, which indicates the similarity between the sample X1 and the sample X2, can be represented as $(\delta 11-\delta 21)^2+(\delta 12-\delta 22)^2+(\delta 13-\delta 23)^2+ \ldots +(\delta 1n-\delta 2n)^2$, for example.

Hierarchical cluster analysis can be performed by assuming that the shorter is the inter-vector distance, the higher is the degree of similarity.

Not all of the fitting parameters need to be used, and just the gain set for each frequency may be used, for example. That is, it is possible to use just the amount of change produced by fine adjustment of the gain of the five frequencies (250, 500, 1 k, 2 k, and 4 k hertz) of the sample X1.

Fitting

The hearing aid fitting method in Embodiment 1 pertaining to the present invention will now be described.

Figure 4:
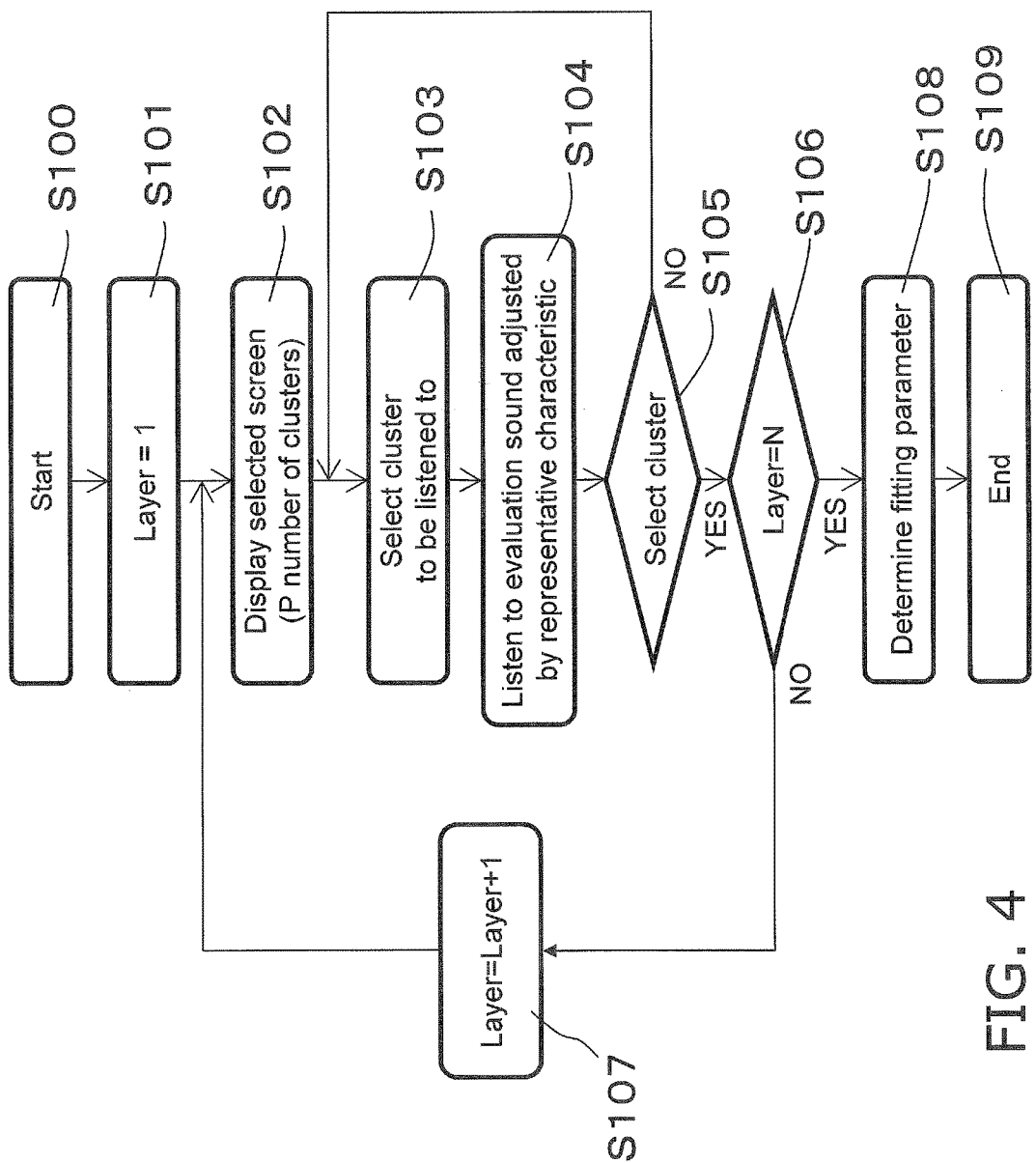
FIG. 4 is a flowchart of a hearing aid fitting method in Embodiment 1 of the present invention.

FIG. 4 is a flowchart of the hearing aid fitting method in this embodiment. As shown in FIG. 4, the operating procedure of the hearing aid fitting device in this embodiment is as follows.

In this embodiment, the initial fitting parameters for the user 7 are found ahead of time, and the keyboard 3 and the mouse 4 are used to register them in the memory 10 of the fitting device 1 in advance.

In finding the initial fitting parameters, hearing ability data for the user is measured from low- to high-pitched sounds in the audible frequency band, and the initial fitting parameter values corresponding to the hearing ability data for the user 7 are found by using NAL-NL1 or another such initial adjustment method in the first fit. Measuring hearing ability in this way is the norm, but if there is no environment for measuring hearing ability, then typical hearing ability data may be readied in advance by broad classification such as mild hearing loss, moderate hearing loss, and severe hearing loss, and the values of the initial parameters may be found by using NAL-NL1 or another such initial adjustment method on the basis of this hearing ability data. That is, even in the absence of an environment for measuring hearing ability, the initial fitting parameters can be found merely by selecting the degree of hearing loss felt by the user 7 himself.

In the above description, the values of the inner peripheral faces for the user 7 determined are registered in the fitting device 1 ahead of time by using the keyboard 3 and the mouse 4, but the fitting device 1 may find them using NAL-NL1 or another such method, on the basis of hearing ability data for the user.

With the fitting method in this embodiment, once fitting is commenced in S100, first the layer (an example of a hierarchical level) is set to 1 in S101.

Figure 5:
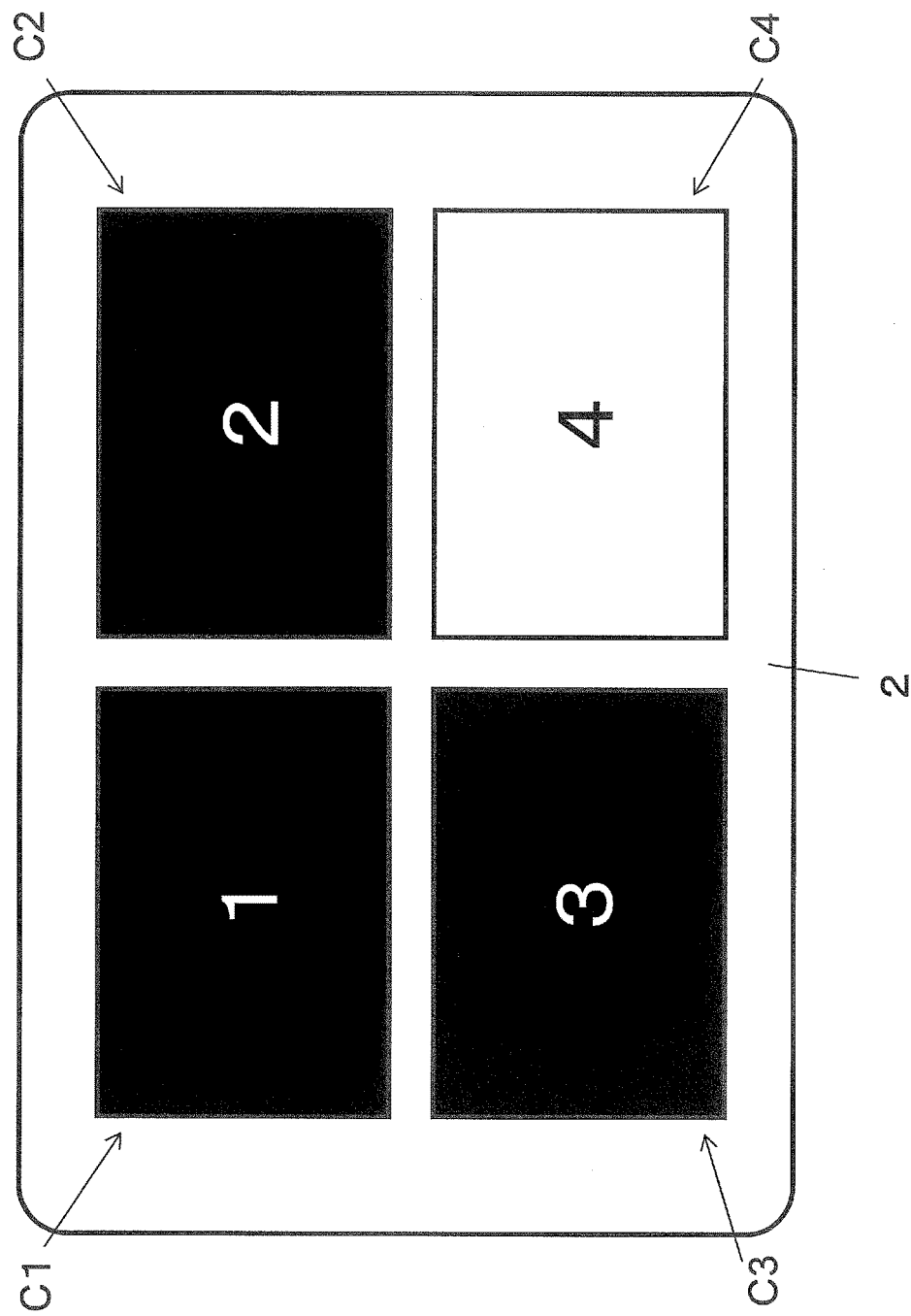
FIG. 5 is a diagram illustrating the hearing aid fitting method in Embodiment 1 of the present invention.

Then, a screen for selecting which cluster to select from among the clusters C1 to C4 is displayed on the display component 2 in S102 (see FIG. 5). In FIG. 5, P is set to 4 in S101. The display component 2 displays information and symbols (the 1, 2, 3, and 4 shown in FIG. 5) and so forth (an example of information related to classification) showing the clusters C1 to C4 in order to select a cluster.

Figure 7:
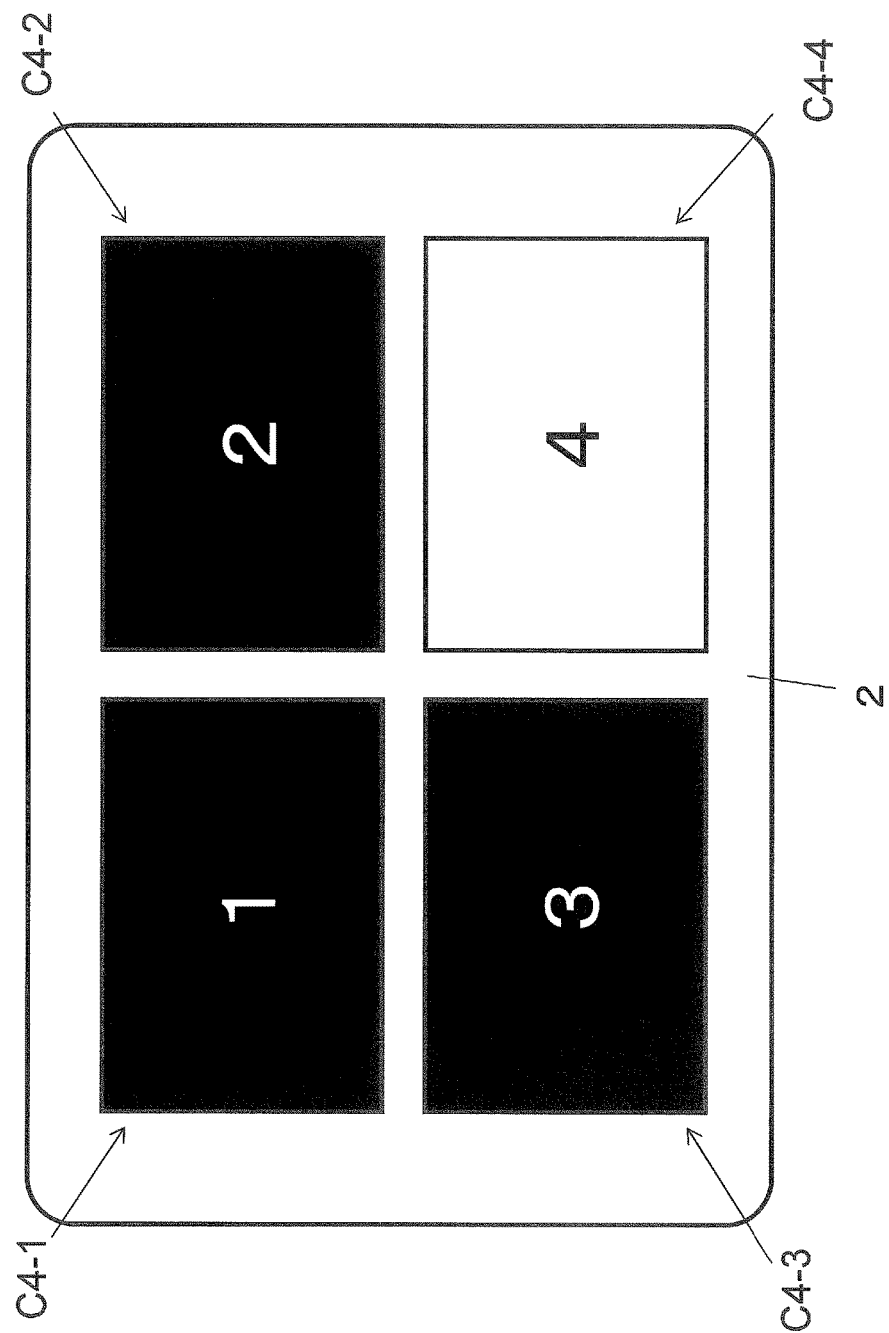
FIG. 7 is a diagram illustrating the hearing aid fitting method in Embodiment 1 of the present invention.
Figure 8:
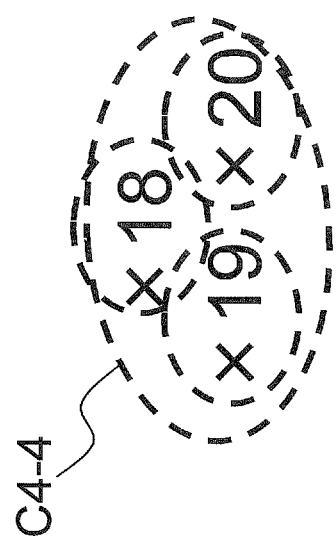
FIG. 8 is a diagram illustrating the hearing aid fitting method in Embodiment 1 of the present invention.
Figure 9:
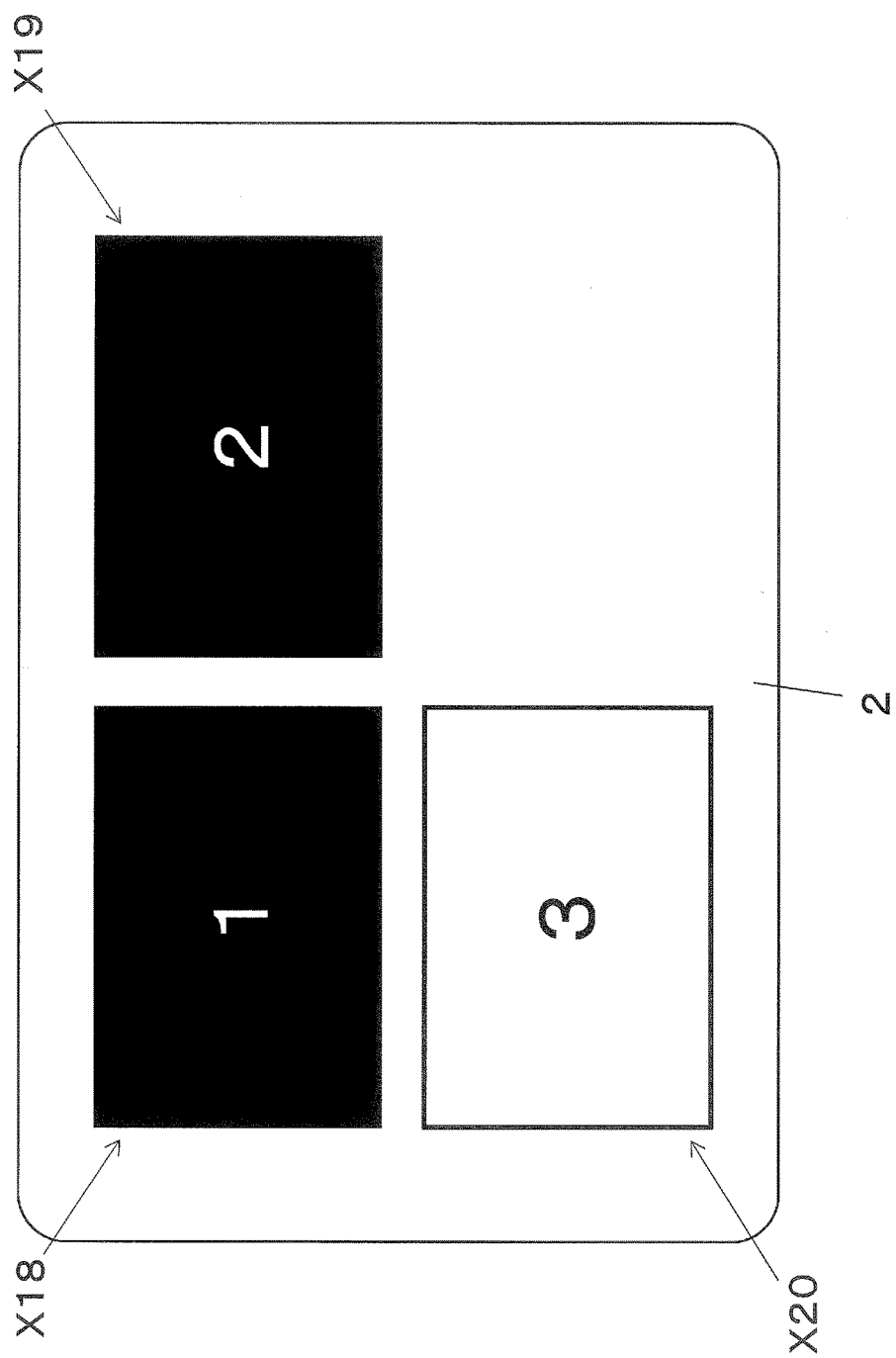
FIG. 9 is a diagram illustrating the hearing aid fitting method in Embodiment 1 of the present invention.

Then, in S103, the user 7 uses the keyboard 3 or the mouse 4 to select one of the clusters in order to perform a hearing test with evaluation audio. Alternatively, in FIG. 5 it is shown that the number surrounded by white has been selected (the same applies to FIGS. 7 and 9 (discussed below)).

Then, in S104, an evaluation sound that reflects the amount of adjustment, which is a representative characteristic of the selected cluster, for the hearing ability data of the user 7 is reproduced from the hearing aid 6. The user 7 listens to and compares the evaluation sounds of clusters C1 to C4, and in S105 selects the cluster to which the representative characteristic thought to be best belongs. Specifically, S103 and S104 will be repeated until the cluster thought to be best is selected in S105, so the evaluation sounds in all of the clusters can be listened to and compared.

Here, if the cluster C1 has been selected as the cluster to be listened to in S103, since the representative characteristic of the cluster C1 is X3, the adjustment difference data is ($\delta$31, $\delta$32, $\delta$33, ..., 3n) and. If we let the initial adjustment data of the user 7 be (S1, S2, S3, ..., Sn) the evaluation sounds of the cluster C1 are sounds in which (S1+$\delta$31, S2+$\delta$32, S3+$\delta$33, ..., Sn+$\delta$3n) have been adjusted as the amount of adjustment. Similarly, since the representative characteristic of the evaluation sound of the cluster C2 is X11, the result is sounds in which (S1+$\delta$111, S2+$\delta$112, S3+$\delta$113, ..., Sn+$\delta$11n) have been adjusted as the amount of adjustment. In the cluster C3, the representative characteristic is X0, so the evaluation sounds are sounds in which (S1, S2, S3, ..., Sn) have been adjusted as the amount of adjustment. With the evaluation sounds in the cluster C4, since the representative characteristic is X15, the result is sounds in which (S1+$\delta$151, S2+$\delta$152, S3+$\delta$153, ..., Sn+$\delta$15n) have been adjusted as the amount of adjustment.

Thus, in the first hierarchical level, if one of a priority order clusters is selected in that hierarchical level, in S106 it is determined whether or not Layer=N, and if it is not N, Layer is incremented in S107. That is, control proceeds to cluster selection in the second layer. Since it is defined that N=3 in the this embodiment, if cluster selection is performed in the third hierarchical level, control proceeds from S106 to S108.

To describe this in greater detail, in clusters C1 to C4 of the first layer, if the cluster C4 is selected, for example, the optimal cluster will then be selected in steps S102 to S105 from among a further classification of this cluster C4 in the second level. FIG. 6 shows the classification of the cluster C4, in which X14 and X15 are classified to cluster C4-1, X16 to cluster C4-2, X17 to cluster C4-3, and X18, X19, and X20 to cluster C4-4. The representative characteristics of these clusters are located in the approximate center of each cluster, with cluster C4-1 being X14, cluster C4-2 being X16, cluster C4-3 being X17, and cluster C4-4 being X20. If a sample is located in the approximate center of a cluster, it means that the same has the fine adjustment data closest to the average of the fine adjustment data for all of the samples belonging to that cluster. If just one set of data belongs to a cluster, then that sample will be the representative characteristic. And if two samples belong to a cluster, since their similarity to the average value will be the same, the sample that is closest to X0, for example, may be used as the representative characteristic.

More specifically, in S102 the display unit 2 (see FIG. 7) displays a the screen for selecting from among the clusters C4-1 to C4-4, and in S103 the user 7 uses the keyboard 3 or the mouse 4 to select one of these clusters. Then, in S104 the hearing aid 6 reproduces an evaluation sound that reflects the amount of fine adjustment, which is the representative characteristic of the selected cluster, for the hearing ability data of the user 7. The user 7 listens to and compares the evaluation sounds of the clusters C4-1 to C4-4 in S105, and selects the one thought to be best. In FIG. 6, X20, which is bounded by the line Q, is selected. This operation is the same as for the first hierarchical level, and will therefore not be described again.

If the cluster C4-4 is selected here, then the user 7 performs a listening comparison related to X18, X19, and X20 (see FIG. 7) that are classified to this cluster C4-4.

Since we are currently at the second hierarchical level, control proceeds from S106 to S107, and Layer=3. Then, in the third hierarchical level, the control of S102 to S105 is performed, and cluster selection is carried out.

More specifically, in S102 the display unit 2 (see FIG. 9) displays a the screen for selecting from among the clusters C4-4-1 to C4-4-3, and in S103 the user 7 uses the keyboard 3 or the mouse 4 to select one of these clusters. In this embodiment, only X18 belongs to the cluster C4-4-1, only X19 belongs to the cluster C4-4-2, and only X20 belongs to the cluster C4-4-3.

Then, in S104 the hearing aid 6 reproduces evaluation sounds that reflect the amount of fine adjustment, which is a representative characteristic, set for the selected cluster. The user 7 listens to and compares the evaluation sounds of X18 to X20 in S105, and selects the one that is thought to be best.

Then, in S106, since currently Layer=3, and N is set to 3 in this embodiment, control proceeds to S108, and the representative characteristic of the cluster that was finally selected is determined as the final fine adjustment data for the user 7 (the values of the fitting parameter in fine adjustment).

The sum of adding the fine adjustment data to the initial adjustment data serves as the final adjustment data used in the hearing aid 6.

The clusters thus classified are systematically followed in order, so that the representative characteristic that is ultimately arrived at becomes the fine adjustment value for the user 7. This is only possible by classifying fine adjustments extracted from past adjustment data into hierarchical levels as in this embodiment. In general, steadily narrowing down from broader to narrower classifications is the method that is commonly used for the menus of DVD recorders, for example. However, in the adjustment of a hearing aid, how to produce the hierarchy has been just as difficult a challenge as it is to acquire know-how in fine adjustment.

The above-mentioned problem was solved by using the fitting results of other patients as a difference value from the initial adjustment amount (reference adjustment amount) found from a fitting theory such as NAL-NL1, and then hierarchically classifying the results. For example, the optimal adjustment can be chosen from among fine adjustment data for 200 patterns by having the patient listen to and compare four hierarchical levels at most, that is by listening to and comparing the adjustment values for 4×4=16 patterns.

Also, efficient search is difficult with a conventional method using a genetic algorithm, since the search for parameters is carried out mechanically, regardless of fitting know-how in recombination or mutation, but with the method of the present invention, since the parameter search is itself a reflection of fitting patterns gleaned from past fitting instances, this is linked to better efficiency in the adjustment work, that is, to adjustment that takes less time.

Features (1)

The fitting device 1 in this embodiment comprises the hierarchically classified database 12 (an example of a database) and the adjustment data determination component 20. A plurality of sets of adjustment difference data (an example of previously acquired adjustment data) obtained by hearing aid fitting are stored in the hierarchically classified database 12 after being hierarchically classified according to their similarity in the amount of adjustment. The adjustment data determination component 20 determines the fine adjustment data (an example of adjustment data) for a hearing aid by selecting one cluster out of a plurality of clusters (an example of classification) in various hierarchical levels.

Consequently, the fine adjustment data for the hearing aid can be determined on the basis of adjustment difference data that has been hierarchically classified according to its similarity in the amount of adjustment, so fewer listening comparisons are required, and the fitting work can be carried out more efficiently.

(2)

Also, with the fitting device 1 in this embodiment, the adjustment amount is the difference between the final adjustment data that is finally determined in the fitting of the hearing aid, and the initial adjustment data obtained by a specific initial adjustment method.

Consequently, the adjustment difference data can be hierarchically classified by using a difference value, which is the amount of fine adjustment from the initial adjustment data obtained by initial fitting. Accordingly, the fine adjustment work after initial fitting of a hearing aid can be carried out more efficiently by following a hierarchy.

(3)

Also, with the fitting device 1 in this embodiment, the adjustment data determination component 20 comprises the connector 9 (an example of a transmitter). The connector 9 sends a representative characteristic (an example of representative adjustment data that represents classification) to the hearing aid 6. The adjustment data determination component 20 has the selector 19. The selector 19 selects one of the clusters in each hierarchical level according to the evaluation audio emitted from the hearing aid 6 that has been adjusted on the basis of the representative characteristic.

Consequently, a cluster can be selected on the basis of an evaluation sound, and the fitting work can be carried out more efficiently.

(4)

As shown in FIG. 3, with the fitting device 1 in this embodiment, the representative characteristic is adjustment difference data that is most similar to the average value of all of the adjustment difference data included in the cluster.

This allows fitting to be performed and evaluation sounds to be outputted according to the most average adjustment difference data in the classification, which makes it possible to perform the fitting work efficiently.

(5)

Also, the adjustment data determination component 20 of the fitting device 1 in this embodiment further has the display component 2 that displays information related to clusters in each of the hierarchical levels in order to select a cluster.

Consequently, selection candidate clusters displayed on the display component 2 can be selected with the keyboard 3 or the mouse 4 (an example of a selector), so there is less hesitation on the part of the user, and as a result the adjustment work is more efficient, that is, the adjustment takes less time.

(6)

The hearing aid fitting method in this embodiment is a hearing aid fitting method that makes use of a hierarchically classified database 12 in which a plurality of sets of adjustment difference data obtained by a hearing aid fitting method are stored after being hierarchically classified according to their similarity in amount of adjustment, wherein said method comprises steps S100 to S109 (an example of an adjustment data determination step). In S100 to S109 (an example of an adjustment data determination step), adjustment data is determined for the hearing aid 6 by selecting one of the plurality of clusters in each hierarchical level.

Consequently, fine adjustment data for the hearing aid can be determined on the basis of the adjustment difference data hierarchically classified according to similarity in amount of adjustment, so fewer listening comparisons are required, and the fitting work can be carried out more efficiently.

(7)

Also, steps S100 to S109 (an example of adjustment data determination steps) in the hearing aid fitting method in this embodiment have S104 (an example of a test sound output operation) in which adjustment is performed on the hearing aid 6 on the basis of a representative characteristic (an example of representative adjustment data) that represents each of a plurality of clusters in each hierarchical level, and an evaluation sound (an example of a test sound) is outputted from the adjusted hearing aid 6, S105 (an example of a selection operation) in which one of the plurality of clusters is selected in each hierarchical level on the basis of the evaluation sound, and S102 to S108 (an example of a repetition operation) in which S104 (an example of an evaluation sound output operation) and S105 (an example of a selection operation) are repeated to determine fine adjustment data (an example of adjustment data) for the hearing aid 6.

Consequently, a cluster can be selected on the basis of evaluation sounds, and fitting work can be carried out more efficiently.

(8)

Steps S100 to S107 (an example of adjustment data determination steps) in the hearing aid fitting method in this embodiment have S102 (an example of a display operation) in which symbols, information representing a plurality of clusters in each hierarchical level, and so forth (an example of information related to classification) are displayed, and S104 (an example of an evaluation sound output operation) is performed by selecting information related to the cluster displayed with the symbols, information representing a cluster, etc.

Consequently, selection candidate clusters displayed on the display component 2 can be selected with the keyboard 3 or the mouse 4 (an example of a selector), so there is less hesitation on the part of the user, and as a result the adjustment work is more efficient, that is, the adjustment takes less time.

Other Embodiments (A)

In the present invention, a description was given in which adjustment difference values were disposed on a two-dimensional map. With this method, a top-down approach was employed in which first all the data was divided in four, and then each cluster was further divided in four, but this is not the only method possible. In other words, the clustering may be accomplished by any method as long as it allows hierarchical classification. For instance, it is also possible to utilize adjustment difference data compiled by a bottom-up clustering method in which 200 patterns of adjustment difference data are sorted by how close together they are, and clustering is performed in a tree structure.

(B)

Also, in this embodiment the description was based on 200 case patterns of adjustment difference data, but the number is not limited to 200. However, if more data is stored, then more hierarchical levels of listening comparison will be required with actual patients. For example, if data for 1000 cases is stored, which all 1000 patterns are divided into four per hierarchical level, there will be five hierarchical levels, so five hierarchical levels will need to be listened to and compared. However, with deeper hierarchical levels, there will be less difference between the patterns, making it harder to distinguish between sounds.

Specifically, since it is difficult to distinguish between sounds in the comparison test, it is preferable if the listening comparison test can be completed in four hierarchical levels. Accordingly, the actual data for 1000 cases is classified into about 200 cases by bottom-up clustering, for example, and the centroid (average value) of each cluster is found to extract fine adjustment patterns. The hierarchically classified database is preferably configured using patterns for about 200 cases thus extracted.

Also, the frequency (how many of the 1000 cases belong to each pattern of the 200 cases) can be found by extracting these patterns for about 200 cases from the actual data for 1000 cases. That is, the more cases there are that belong, the higher is the frequency at which adjustment results for other patients who underwent fitting in the past will be determined to be favorable and selected. In this embodiment the description was of selecting the pattern closest to the centroid (average) as the representative characteristic of each cluster, but it is even more preferable to base the selection on this frequency. That is, the representative characteristic should be the one with the highest frequency of being selected after being determined preferable in the adjustment results for other patients who underwent fitting in the past, among the adjustment difference data included in each classification. Determination of whether or not a case belongs may be accomplished based on whether or not the case is within a specific range of similarity for each pattern of 200 cases.

Thus, a plurality of sets of adjustment difference data are prioritized according to frequency within each cluster, and the representative characteristic may be the data with the highest priority.

Consequently, fitting and the output of evaluation sounds can be accomplished by means of adjustment data with a high priority, so the fitting work can be carried out more efficiently.

(C)

It is preferable if the adjustment difference data of the 200 patterns described in the above embodiment includes fitting data for people whose hearing ability data is similar to the hearing ability data of the current user 7. Specifically, in the extraction of patterns for about 200 cases from the actual data of 1000 cases as in the example discussed in (B) above, if cases having hearing ability data with a high degree of similarity to the hearing ability data of the user 7 are extracted, there will be more existing adjustment difference data applicable to the user in fine adjustment after initial fitting, so the hearing aid fitting can be performed more accurately.

(D)

Also, in the above embodiment, adjustment difference data was described as an example of previously acquired adjustment data, and the hierarchically classified database 12 had adjustment difference data for each sample, but this is not limited to adjustment difference data, and there may also be initial adjustment data produced by initial fitting for each sample. In this case, an example of previously acquired adjustment data corresponds to adjustment difference data and initial adjustment data.

(E)

Also, in the above embodiment, the representative characteristic was adjustment difference data that was the most similar to the average value for all of the adjustment difference data included in a cluster, but the average value itself may also be used as a representative characteristic.

(F)

Also, in the above embodiment, the description was of performing hierarchical cluster analysis in which the shorter was the inter-vector distance when adjustment difference data was vector displayed, the higher was the similarity, but as in Embodiment 3 below, hierarchical cluster analysis may be performed in which similarity is proportional to how small is the sum of the different values for the various parameters of the adjustment difference data. More specifically, the sum of the difference between the sample X1 and the sample X2 can be expressed as $(\delta 11 - \delta 21) + (\delta 12 - \delta 22) + (\delta 13 - \delta 23) + \ldots + (\delta 1n - \delta 2n)$.

Embodiment 2

Next, the hearing aid in Embodiment 2 pertaining to the present invention will be described.

The hearing aid in Embodiment 2 is configured so that the above-mentioned fitting can be performed at the hearing aid. With this configuration, the result obtained in the above embodiment can be realized without the use of a fitting device.

Configuration of Hearing Aid 21

Figure 10:
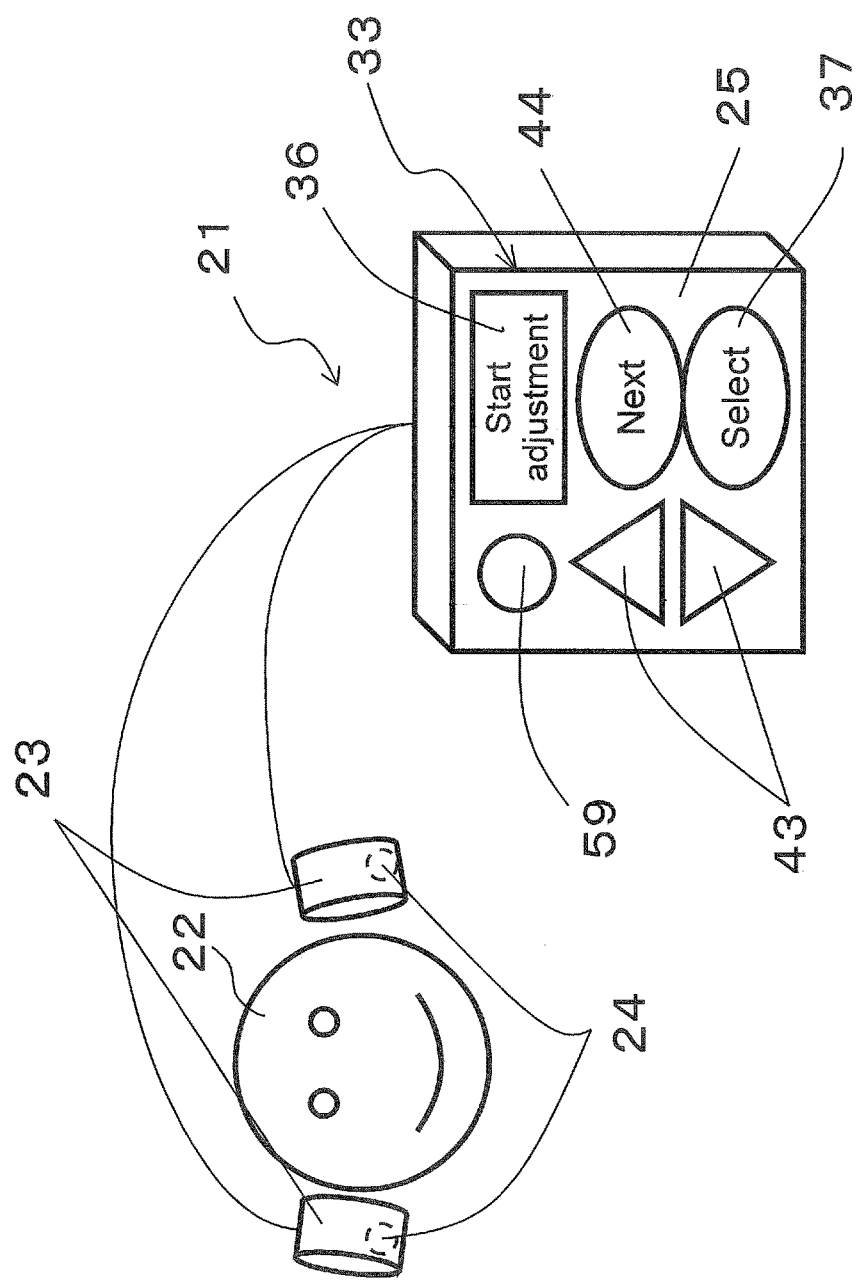
FIG. 10 is a diagram of the usage state of the hearing aid in Embodiment 2 of the present invention.

FIG. 10 shows the hearing aid 21 in Embodiment 2. As shown in FIG. 10, the hearing aids 21 are mounted in the ear holes (not shown) of the hearing aid wearer 22.

As shown in FIG. 10, these hearing aids 21 comprise earphones 23 that are worn by being hooked over the upper part of the ears of the hearing aid wearer 22 and that emit sounds toward the ear holes (not shown) of the hearing aid wearer 22, microphones 24 that are disposed facing the opposite side from the hearing aid wearer 22 in a state in which the earphones 23 have been placed on the ears of the hearing aid wearer 22, and body cases 25 that are connected by wire or wirelessly to the earphones 23.

Figure 11:
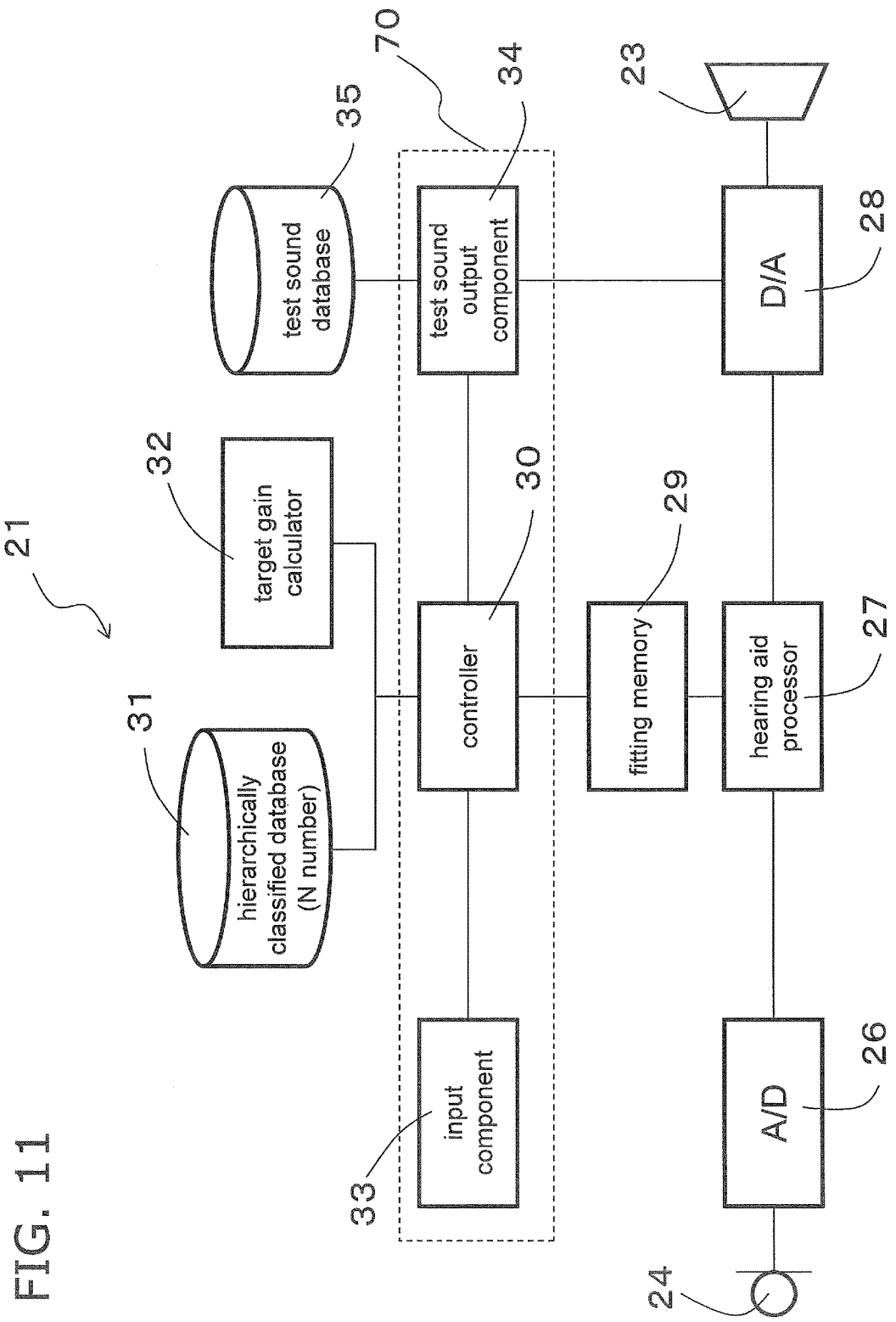
FIG. 11 is a block diagram of the hearing aid in Embodiment 2 of the present invention.

FIG. 11 is a control block diagram of the hearing aids 21 in Embodiment 2. As shown in FIG. 11, each hearing aid 21 comprises an earphone 23, a microphone 24, an A/D converter 26, a hearing aid processor 27, a D/A converter 28, a fitting memory 29, an adjustment data determination component 70, a hierarchically classified database 31, a target gain calculator 32, and a test sound database 35.

As shown in FIG. 11, the microphone 24 is connected via the A/D converter 26 to the hearing aid processor 27, and the earphone 23 is connected via the D/A converter 28 to the hearing aid processor 27. The hearing aid processor 27 subjects sound digitized by the A/D converter 26 to hearing aid processing suited to the hearing aid wearer 22, and sends the result to the D/A converter 28. The sound that has undergone analog conversion by the D/A converter 28 is sent from the earphone 23 to the hearing aid wearer 22.

The adjustment data determination component 70 also has an input component 33, a controller 30, and a test sound output component 34. The controller 30 is connected to the hierarchically classified database 31 and the target gain calculator 32, and the test sound output component 34 is connected to the test sound database 35.

The hearing aid processor 27 is connected to the fitting memory 29 (memory component), which stores adjustment data for the hearing aid 21. This fitting memory 29 is connected via the controller 30 to the hierarchically classified database 31, the target gain calculator 32, and the input component 33.

The hierarchically classified database 31 here stores the adjustment difference data described in Embodiment 1 above after classifying it into hierarchical levels. Specifically, a plurality of sets of previously acquired adjustment data are divided into a plurality of adjustment classifications, and these adjustment classifications are hierarchically stored in the hierarchically classified database 31. This will be described in detail below.

The controller 30 is also connected to the test sound output component 34, and is connected to the test sound database 35 and the D/A converter 28 via this test sound output component 34.

The test sound database 35 here stores test sound data for testing the hearing ability of the hearing aid wearer 22. The test sound data is sound data at each frequency, such as 250, 500, 1 k, 2 k, and 4 k hertz (Hz). This test sound data is sent through the test sound output component 34 to the D/A converter 28, where it is converted into an analog audio signal, after which it is outputted from the earphone 23 as a test sound.

The target gain calculator 32 calculates the various values of the fitting parameters in initial fitting using a fitting theory. The gain is calculated for each frequency such as 250, 500, 1 k, 2 k, and 4 k hertz (Hz), according to the hearing ability data for the hearing aid wearer 22.

That is, the hearing aid 21 in this embodiment uses the target gain calculator 32 to perform initial adjustment of the fitting on the hearing aid wearer 22, and then uses the hierarchically classified database 31 to perform fine adjustment of the fitting on the hearing aid wearer 22, which allows the fitting for the hearing aid wearer 22 to be completed by the hearing aid 21 itself.

As shown in FIGS. 10 and 11, the input component 33 has an adjustment start button 36, a select button 37, a switch button 43, an enter button 44, and an option select button 59. The adjustment start button 36 is used to start initial fitting and fine adjustment on the hearing aid wearer 22. The select button 37 is used to end fine adjustment. The switch button 43 is used when switching the classification in the first hierarchical level (discussed below). The enter button 44 is used in determining the classification in each hierarchical level. The option select button 59 is used for making a selection in accordance with any options that are used, such as ear tips.

The controller 30 receives input from the input component 33 and controls the fitting according to a program stored in the memory of the controller 30.

Hierarchically Classified Database 31

Next, the hierarchically classified database 31 will be described.

Figure 13:
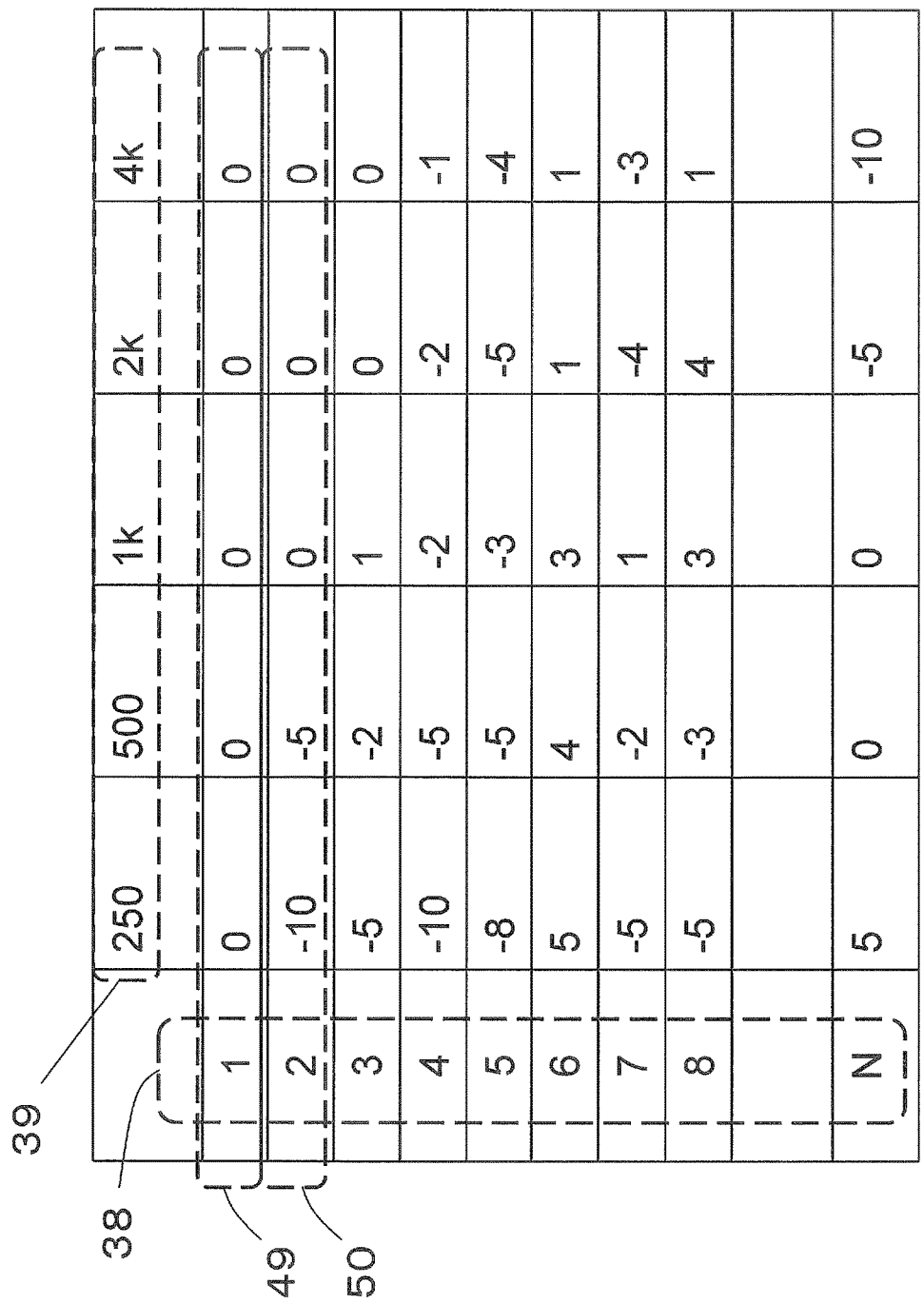
FIG. 13 is a diagram illustrating the hearing aid fitting method in Embodiment 2 of the present invention.

FIG. 13 shows the adjustment difference data stored in the hierarchically classified database 31. The adjustment difference data (an example of previously acquired adjustment data) shown in FIG. 13 shows how much the gain in the final adjustment data has changed for each frequency from the initial adjustment data in the initial fitting. In other words, this represents the difference between the gain of the parameters for the final adjustment data and the gain of the parameters for the initial adjustment data at each frequency. Column 38 in FIG. 13 is the number of the adjustment difference data, while the headings 39 are the frequency. For example, the adjustment difference data in number 2 has a gain that is 10 lower than the initial parameter at a frequency of 250 Hz.

Figure 14:
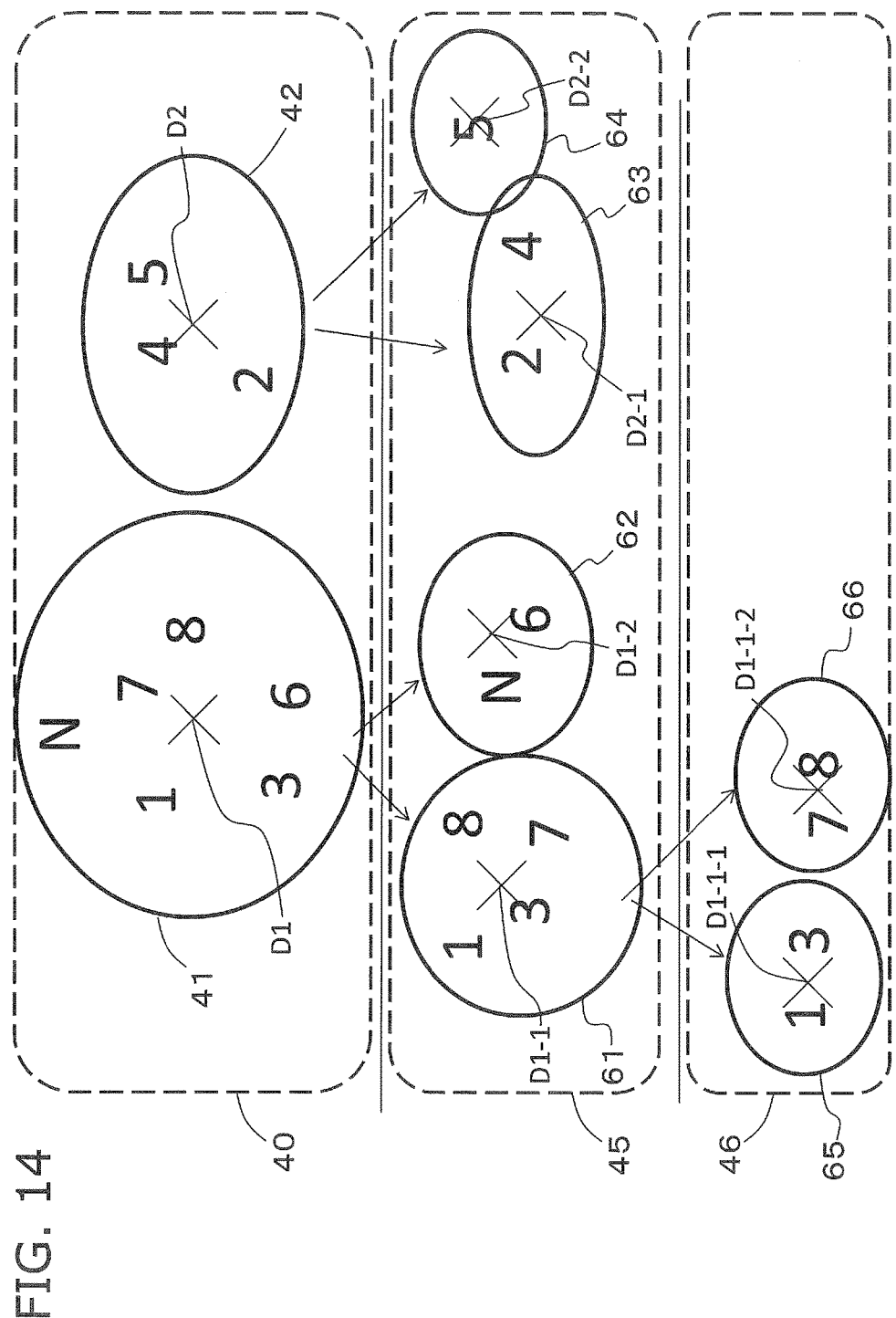
FIG. 14 is a diagram illustrating the hearing aid fitting method in Embodiment 2 of the present invention.

FIG. 14 shows the hierarchical classification in this embodiment. In producing the above-mentioned hierarchically classified database from the adjustment difference data 1 to N, the adjustment difference data 1 to N are classified according to similarity, just as in Embodiment 1.

As shown in FIG. 14, these sets of adjustment difference data from 1 to N are classified after being divided into hierarchical levels, and then stored in the hierarchically classified database 31 shown in FIG. 11. For example, in this embodiment a first hierarchical level 40 is divided in two. Six sets of adjustment difference data (numbers 1, 3, 6, 7, 8, and N) are classified to the first classification 41 of the first hierarchical level 40, and three sets of adjustment difference data (numbers 2, 4, and 5) are classified to a second classification 42. The adjustment difference data sets from 9 to N-1 are not shown in the drawing.

The hearing aid wearer 22 listens to the evaluation sounds of the representative characteristics of each classification, and selects the one that is best. This representative characteristic may be, for example, the average value for each frequency of the adjustment difference data included in each classification. In FIG. 14, D1 is the representative characteristic of the first classification 41, and D2 is the representative characteristic of the second classification 42. More specifically, with the second classification 42, for example, the adjustment difference data numbers 2, 4, and 5 belong to the second classification 42. The difference from the gain of the initial fitting in the adjustment difference data numbers 2, 4, and 5 at a frequency of 250 Hz is −10, −10, and −8, respectively, so the average is approximately −9.3. This results in a difference at 250 Hz in the representative characteristic D2 of −9.3. When calculations are similarly made at the other frequencies, the difference values at each frequency (250, 500, 1 k, 2 k, and 4 k Hz) for the representative characteristic D2 are −9.3, −5, −1.7, −2.3, and −1.7.

As shown in FIG. 14, in a second hierarchical level 45, the first classification 41 and the second classification 42 are divided into two classifications each. The first classification 41 is divided into a 1-1$^{th}$ classification 61 and a 1-2$^{th}$ classification 62, while the second classification 42 is divided into a 2-1$^{th}$ classification 63 and a 2-2$^{th}$ classification 64. The adjustment difference data numbers 1, 3, 7, and 8 belong to this 1-1$^{th}$ classification 61, and the representative characteristic thereof is indicated as D1-1. The adjustment difference data of numbers 6 and N belong to the 1-2$^{th}$ classification 62, and the representative characteristic thereof is indicated as D1-2. Meanwhile, the adjustment difference data numbers 2 and 4 belong to the 2-1$^{th}$ classification 63, and the representative characteristic thereof is indicated by D2-1. The adjustment difference data number 5 belongs to the 2-2$^{th}$ classification 64, and the representative characteristic thereof is indicated by D2-2. Since the 2-2$^{th}$ classification 64 includes only the adjustment difference data number 5, the adjustment difference data number 5 is the representative characteristic of the 2-2$^{th}$ classification 64.

Furthermore, in a third hierarchical level 46, the 1-1$^{th}$ classification 61 is divided into a 1-1-1$^{th}$ classification 65 and a 1-1-2$^{th}$ classification 66. The adjustment difference data numbers 1 and 3 belong to the 1-1-1$^{th}$ classification 65, and the representative characteristic thereof is indicated as D1-1-1. The adjustment difference data numbers 7 and 8 belong to the 1-1-2$^{th}$ classification 66, and the representative characteristic thereof is indicated as D1-1-2.

With this embodiment thus configured, the following procedure is executed to perform fitting on the hearing aid wearer 22 at the hearing aid 21 shown in FIG. 10.

Fitting

Figure 12:
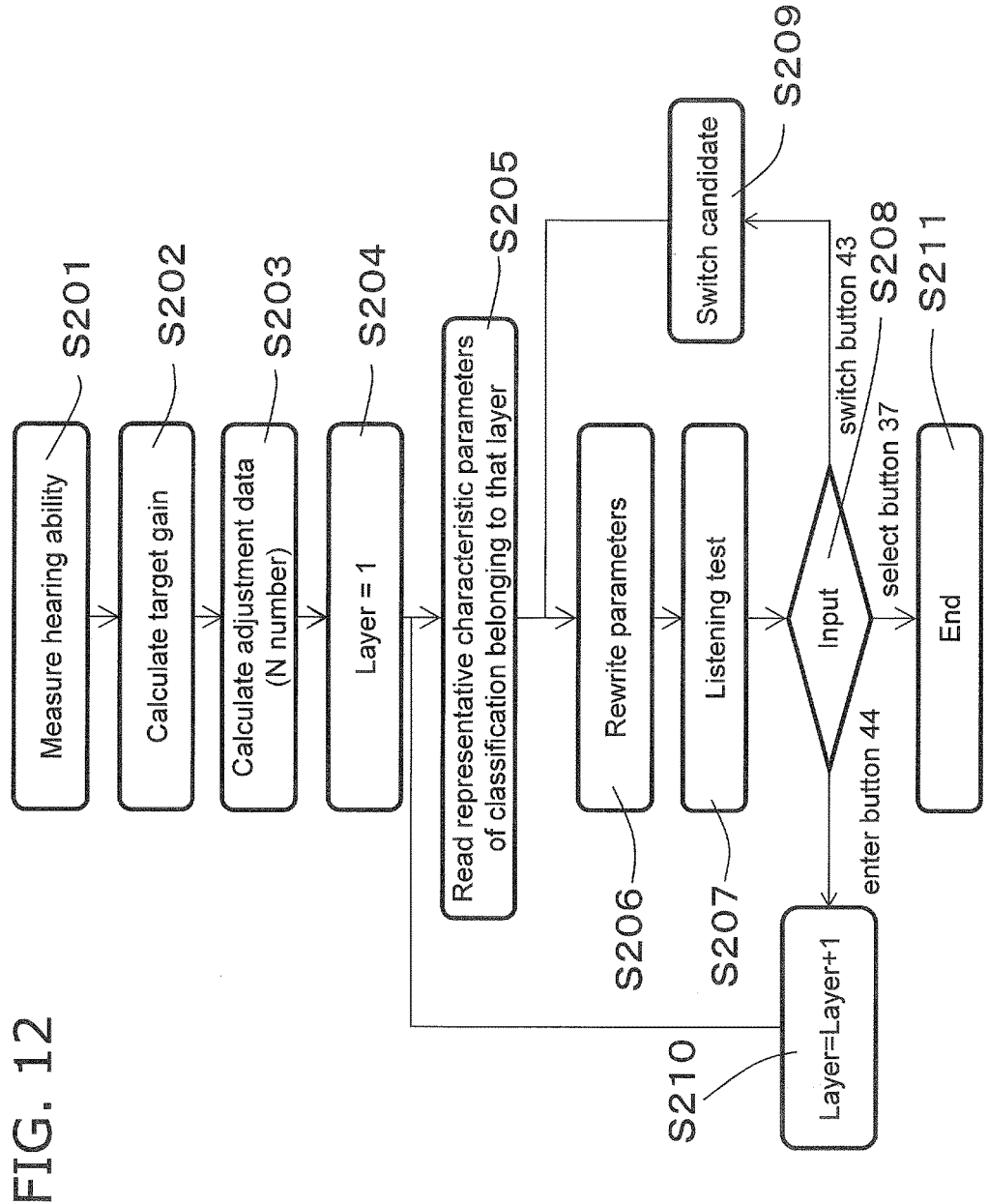
FIG. 12 is a flowchart of a hearing aid fitting method in Embodiment 2 of the present invention.

FIG. 12 is a flowchart of the hearing aid fitting method in this embodiment.

First, the adjustment start button 36 provided to the body case 25 of the hearing aid 21 is pressed to start the fitting for the hearing aid wearer 22 (S201 in FIG. 12).

When the adjustment start button 36 is pressed, in S202 the controller 30 outputs a test sound from the earphone 23 to perform initial fitting using a fitting theory. More specifically, test sound data stored in the test sound database 35 for each frequency of 250, 500, 1 k, 2 k, and 4 k hertz (Hz), for example, is sent through the test sound output component 34 to the D/A converter 28. The test sound data is then converted into analog audio signals, after which these are successively outputted as test sounds from the earphone 23 for each frequency.

If the hearing aid wearer 22 is able to hear a test sound, he presses the select button 37, which allows the hearing aid wearer 22 to give feedback to the effect that he has heard that test sound. Upon receipt of this feedback, the hearing aid 21 outputs a test sound corresponding to the next frequency from the earphone 23.

Here, the order in which the test sounds are outputted may start from the one with the lowest frequency, or may start from the highest frequency. Also, a predetermined order may be set irregularly and outputted. Each test sound may be outputted only once, or a sound may be outputted a number of times corresponding to the same frequency. That is, some measure may be taken to eliminate bias or determination error on the part of the hearing aid wearer 22, so as to obtain a more accurate determination result.

If the hearing aid wearer 22 can not hear a test sound, then he will make no input, so the controller 30 performs control so as to output the test sound corresponding to the next frequency from the earphone 23 after a specific amount of time has passed.

This operation is repeated to obtain measurement results for the hearing ability of the hearing aid wearer 22 at each of the frequencies of 250, 500, 1 k, 2 k, and 4 k (Hz). Specifically, hearing ability data for the hearing aid wearer 22 is obtained.

When hearing ability data for the hearing aid wearer 22 is obtained, the target gain calculator 32 finds the initial fitting parameters corresponding to the hearing ability data for the hearing aid wearer 22 using an initial adjustment method such as NAL-NL1 as the initial fitting described in Embodiment 1 above, adjusts the hearing aid characteristics of the hearing aid 21, and ends the initial fitting (S202 in FIG. 12).

Here, the initial fitting parameters may be found by readying in advance typical hearing ability data by broad categories such as mild hearing loss, moderate hearing loss, and severe hearing loss, and using an initial adjustment method such as NAL-NL1 on the basis of this hearing ability data. With this method, the initial fitting can be easily ended merely by selecting the degree of hearing loss recognized by the hearing aid wearer 22 himself.

When the initial fitting is complete, the hearing aid 21 notifies the hearing aid wearer 22 by sound, etc., that the initial fitting has ended. The audio may be outputted from the earphone 23 of the hearing aid 21, etc.

Next, the hearing aid wearer 22 presses the adjustment start button 36 provided to the body case 25 of the hearing aid 21. This input starts fine adjustment so that the hearing aid wearer 22 can hear better. Here, the adjustment start button 36 also serves to start the fine adjustment, but a separate input button may be provided.

When the adjustment start button 36 is pressed again, a specific number of sets of adjustment data are calculated (S203 in FIG. 12). In this embodiment, the number of sets of adjustment difference data shall be N, and the sets will be numbered from 1 to N. Saying here that the adjustment data is calculated corresponds to producing adjustment data by adding adjustment difference data to the initial adjustment data produced by initial fitting.

First, the layer is set to 1, and the first hierarchical level 40 is selected (S204 in FIG. 12).

Then, the controller 30 reads the values of the various parameters of adjustment difference data for the representative characteristics of the first classification 41 and second classification 42 of the first hierarchical level 40, and the fine adjustment parameters are rewritten (S205 and S206 in FIG. 12). Specifically, we will let the gain at frequencies of 250, 500, 1 k, 2 k, and 4 k (Hz) for the initial adjustment data obtained by initial fitting on the hearing aid wearer 22 be S1, S2, S3, S4, and S5. Since the representative characteristics of the second classification 42 are −9.3, −5, −1.7, −2.3, and −1.7, the evaluation sounds for the second classification 42 are sounds in which the amounts of adjustment are S1-9.3, S2-5, S3-1.7, S4-2.3, and S5-1.7.

Evaluation sound data stored in the test sound database 35 is sent through the test sound output component 34 to the D/A converter 28 according to the rewritten fine adjustment parameters. The evaluation sound data is then converted into an analog audio signal, after which this is outputted as an evaluation sound of the representative characteristic from the earphone 23 of the hearing aid 21, and the hearing aid wearer 22 listens to this evaluation sound (S207 in FIG. 12). Conversation audio, audio of news being read, or the like can be used effectively as the evaluation sound data, and parameters that are better suited to practical use can be selected by adding multiple talker noise, etc.

Next, the hearing aid wearer 22 presses either the up or down switch button 43 provided to the body case 25 of the hearing aid 21 to switch between the first classification 41 and the second classification 42 (S208 and S209 in FIG. 12).

Thus, the hearing aid wearer 22 presses the enter button 44 when he listens to and compares evaluation sounds of the representative characteristics of the first classification 41 and the second classification 42 and deems a classification to be favorable, thereby entering this favorable classification, after which the hierarchical level moves to the next level (S208 and S210 in FIG. 12).

In this embodiment, this move is to the second hierarchical level 45. Listening and comparison are then performed at the second hierarchical level 45 in the same way as when the evaluation sounds were listened to and compared in the first hierarchical level 40 as discussed above, and classifications deemed favorable are entered (S205 in FIG. 12).

This operation is repeated to performing listening and comparison down to the lowest hierarchical level, classifications deemed favorable are entered, and then the select button 37 is pressed to end the fitting (S211 in FIG. 12). In this embodiment, the third hierarchical level 46 is the lowest level, as shown in FIG. 14.

The values for parameters of the representative characteristics thus determined are reflected in the parameter values in the initial fitting on the hearing aid wearer 22, and this determines the fitting parameter values for the final adjustment data. The fitting parameters that are ultimately determined are stored in the fitting memory 29, the hearing aid processor 27 performs hearing aid processing on the audio received by the microphones 24 by using the ultimately determined fitting parameters, and the audio that has undergone this hearing aid processing is outputted from the earphone 23 toward the hearing aid wearer 22.

Thus, in this embodiment, the configuration allows fitting to be performed with just a hearing aid, which means that the effect obtained in Embodiment 1 above can be realized with just a hearing aid, without having to use a fitting device, so the adjustment work is more efficient, that is, the adjustment takes less time.

Also, because no fitting device is required in the fitting, the hearing aid wearer 22 himself can perform the fitting in the comfort of his own home, etc., which greatly improves convenience.

Furthermore, if the hearing aid wearer 22 feels that a sound from the hearing aid 21 is hard to hear, the hearing aid wearer 22 himself can perform fitting right there and then, which improves the satisfaction of the hearing aid wearer 22.

Features (1)

The hearing aid 21 in this embodiment comprises the microphone 24 (an example of a receiver), the adjustment data determination component 70, the hearing aid processor 27, and the earphone 23 (an example of an output component). The microphone 24 receives audio. The adjustment data determination component 70 is connected to the hierarchically classified database 31, in which adjustment difference data (an example of previously acquired adjustment data) obtained by hearing aid fitting is stored after being hierarchically classified according to similarity in the amount of adjustment, and adjustment data for the hearing aid is determined by selecting one of the plurality of classifications in each hierarchical level. The hearing aid processor 27 performs hearing aid processing on the received audio on the basis of the determined adjustment data. The earphone 23 outputs the audio that has undergone hearing aid processing.

Consequently, adjustment data for the hearing aid can be determined on the basis of adjustment difference data that has been hierarchically classified according to similarity in the amount of adjustment, so fewer listening comparisons are required, and the fitting work can be carried out more efficiently.

Also, since fine adjustment can be performed with just the hearing aid, no fitting device needs to be used to perform fine adjustment, so there is no need to visit a retail store just to have fine adjustment performed, which is more convenient for the user. Also, because the user does not have to go to the store, the adjustment work is more efficient, that is, the adjustment takes less time.

(2)

With the hearing aid 21 in this embodiment, the amount of adjustment is the difference between the final adjustment data ultimately determined in the fitting of the hearing aid, and the initial adjustment data obtained by a specific initial adjustment method.

This allows the adjustment difference data to be hierarchically classified by using a difference value that is the amount of fine adjustment from the initial adjustment data obtained in the initial fitting. Accordingly, adjustment work following the initial fitting when a hearing aid is fitted can be carried out more efficiently.

(3)

The adjustment data determination component 70 of the hearing aid 21 in this embodiment has the test sound output component 34 and the input component 33. The test sound output component 34 emits evaluation sounds on the basis of representative characteristics (an example of representative adjustment data) that represent classifications. The input component 33 (an example of a selector) selects one of the classifications on the basis of the emitted sounds.

Consequently, the classification can be selected on the basis of evaluation sounds, and fitting work can be carried out more efficiently.

(4)

With the hearing aid 21 in this embodiment, the specific initial adjustment method is an adjustment method in which a fitting theory is used, and initial adjustment data is data obtained by initial fitting using a fitting theory.

Consequently, initial fitting can be performed by using NAL-NL1 (National Acoustic Laboratories-non-linear 1), NAL-NL2, DSL (Desired Sensation Level) i/o, DSLv5, POGO (Prescription of Gain/Output), FIG. 6, or another such fitting theory. Since searching the adjustment difference data can be carried out hierarchically and efficiently, the fine adjustment to match the hearing of an individual for this initial fitting can be carried out more efficiently.

(5)

The hearing aid 21 in this embodiment further comprises the target gain calculator 32 (an example of an initial adjuster), which performs initial fitting on the basis of the hearing ability of the user of the hearing aid.

Consequently, initial fitting can also be performed with just the hearing aid, so there is no need to make a trip to the store when the user has trouble hearing, etc., which improves convenience.

(6)

The hearing aid fitting method in this embodiment involves the use of the hierarchically classified database 31, in which a plurality of sets of adjustment difference data obtained by a hearing aid fitting method are stored after being hierarchically classified according to similarity in the amount of adjustment, and comprises the steps S201 to S211 (an example of adjustment data determination steps). In S201 to S211 (an example of adjustment data determination steps), adjustment data for the hearing aid 21 is determined by selecting a classification from among a plurality of classifications in each hierarchical level.

Consequently, fine adjustment data for the hearing aid can be determined on the basis of adjustment difference data that is hierarchically classified according to similarity in the amount of adjustment, so fewer listening comparisons are required, and the fitting work can be carried out more efficiently.

(7)

Also, the steps S201 to S211 (an example of adjustment data determination steps) in the hearing aid fitting method in this embodiment have S206 and S207 (an example of a test sound output operation) in which adjustment is performed on the hearing aid 21 on the basis of a representative characteristic (an example of representative adjustment data) that represents each of a plurality of classifications in each hierarchical level, and an evaluation sound (an example of a test sound) is outputted from the adjusted hearing aid 21, S208 (an example of a selection operation) in which one of the classifications is selected from the plurality of classifications in each hierarchical level on the basis of the evaluation sound, and S205 to S210 (an example of a repetition operation) in which S206, S207 (an example of an evaluation sound output operation) and S208 (an example of a selection operation) are repeated to determine fine adjustment data (an example of adjustment data) for the hearing aid 21.

Consequently, one of the classifications can be selected on the basis of evaluation sounds, and fine adjustment data can be determined more efficiently.

Other Embodiments

The specific configuration of the present invention is not limited to the above embodiments, and various modifications and changes are possible without departing from the scope of the invention.

(A)

The adjustment difference data, which is an example of previously acquired adjustment data, may be prioritized in advance among the various adjustment classifications, and the representative characteristics of the hierarchical levels may be determined on the basis of this priority. That is, listening comparisons can be carried more easily by steadily increasing the priority from adjustment data with the highest frequency of being selected after being deemed favorable in the adjustment data process, on the basis of adjustment results for other people who have undergone fitting in the past.

Also, the priority may involve the one with the highest frequency of being selected after being deemed favorable (that is, the one with the highest priority) in the adjustment results for other people who have undergone fitting in the past. To find the frequency of each set of adjustment difference data shown in FIG. 13, a method can be used in which past adjustment data (at least N number) is classified by similarity into N number, and a count is taken of how many cases of past adjustment data are included in each classification. The determination of whether or not a date is included in a classification may be made according to whether or not it falls within a specific range of similarity of the various sets of adjustment difference data.

(B)

In Embodiment 2 above, adjustment difference data was given as an example of previously acquired adjustment data, and the adjustment difference data was data indicating how much the gain changed for each frequency from the gain of the various parameters in initial fitting by fine adjustment, but this is not limited to gain alone. The adjustment difference data in Embodiment 2 may include change amounts for compression, TK, or the like, as with the adjustment difference data discussed in Embodiment 1.

(C)

Also, in the above embodiments, the hierarchically classified database 31 has a gain difference value for each frequency, as the adjustment difference data, but this is not limited to a difference value alone, and may also have initial adjustment data for each set of adjustment difference data. In this case, an example of previously acquired adjustment data corresponds to adjustment difference data and initial adjustment data.

(D)

Also, in the above embodiments, the average value for adjustment difference data belonging to a classification is used as a representative characteristic, but adjustment difference data that is the most similar to the average value may instead be used as the representative characteristic, as in Embodiment 1.

Embodiment 3

In Embodiment 2 above, the configuration was such that the hierarchically classified database 31 was used in the fine adjustment of fitting to the hearing aid wearer 22, but the same effect can be achieved with the configuration in Embodiment 3.

Figure 15:
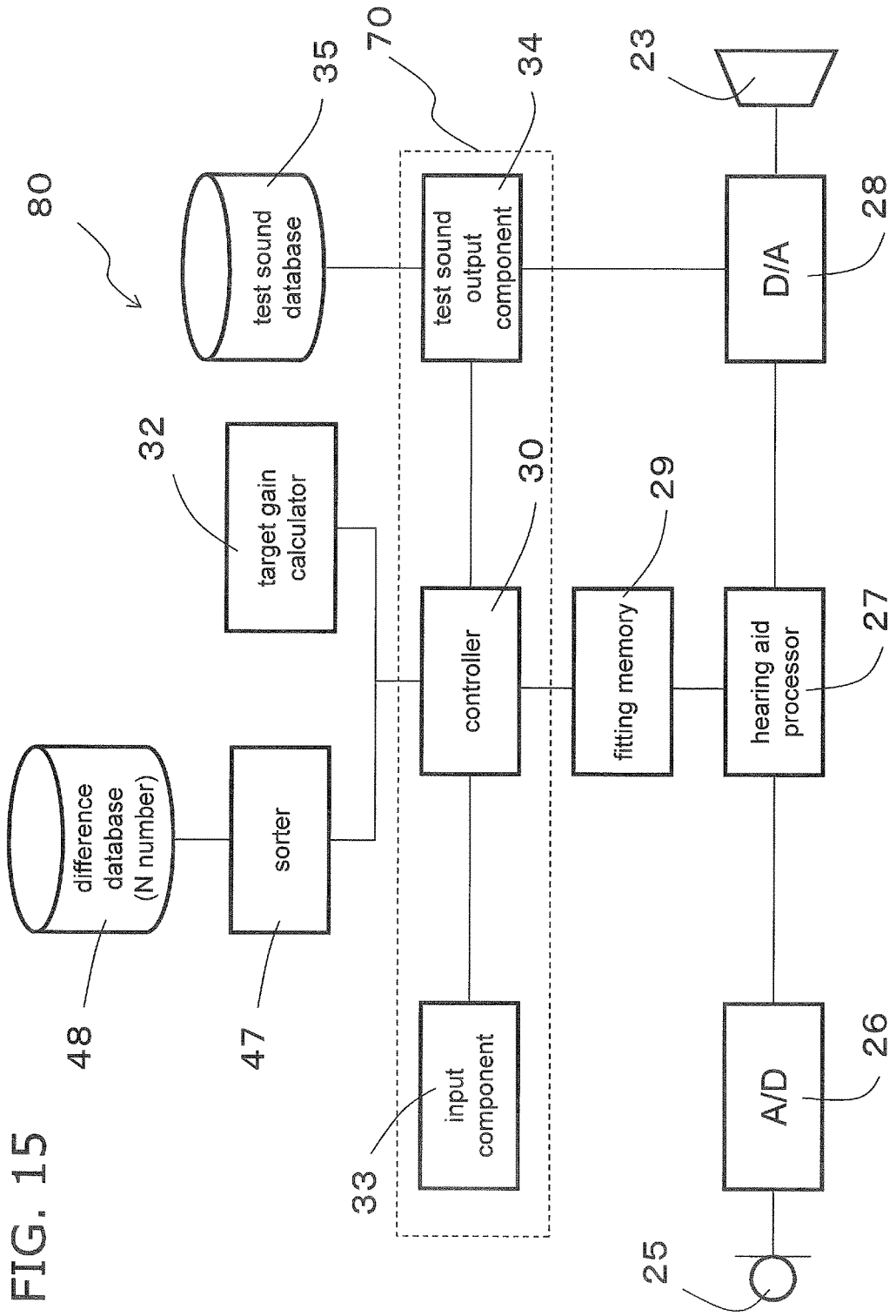
FIG. 15 is a block diagram of the hearing aid in Embodiment 3 of the present invention.

FIG. 15 is a control block diagram of a hearing aid 80 in Embodiment 3. In Embodiment 3 a difference database 48 is connected via a sorter 47 to the controller 30 as shown in FIG. 15, instead of the hierarchically classified database 31 that was connected to the controller 30 in Embodiment 2 above. The external configuration is the same as in FIG. 10 of Embodiment 2, and will therefore not be described again, and in the following description FIG. 10 will substitute as the hearing aid 80 in this embodiment.

FIG. 16 is a diagram illustrating difference database stored in the difference database 48 of this embodiment.

The difference database 48 in this embodiment is composed of the adjustment difference data in FIG. 13 and the similarity database shown in FIG. 16. The similarity database here is such that in the hierarchically classified database 31 shown in FIG. 13 and described in Embodiment 2 above, the sum of the differences in adjustment values of each set of adjustment difference data shown in the column 38 is taken for each of the frequencies shown in the headings 39.

For example, the difference between the first adjustment differential data 49 and the second adjustment differential data 50 shown in FIG. 13 at each frequency is 10 at 250 Hz, 5 at 500 Hz, and 0 at the other frequencies of 1 k, 2 k, and 4 k Hz, so the sum is 15 as shown in the region 51 in FIG. 16. The results of similarly calculating for other combinations of adjustment difference data are stored in the difference database 48. Specifically, the difference database 48 stores the sum of the increases and decreases from the initial fitting that result from fine adjustment at each parameter.

The smaller is a numerical values in this difference database 48, the more similar are two compared sets of adjustment difference data. That is, the higher is the similarity.

The sorter 47 sorts according to the degrees of similarity stored in the similarity database stored in the difference database 48.

Figure 17:
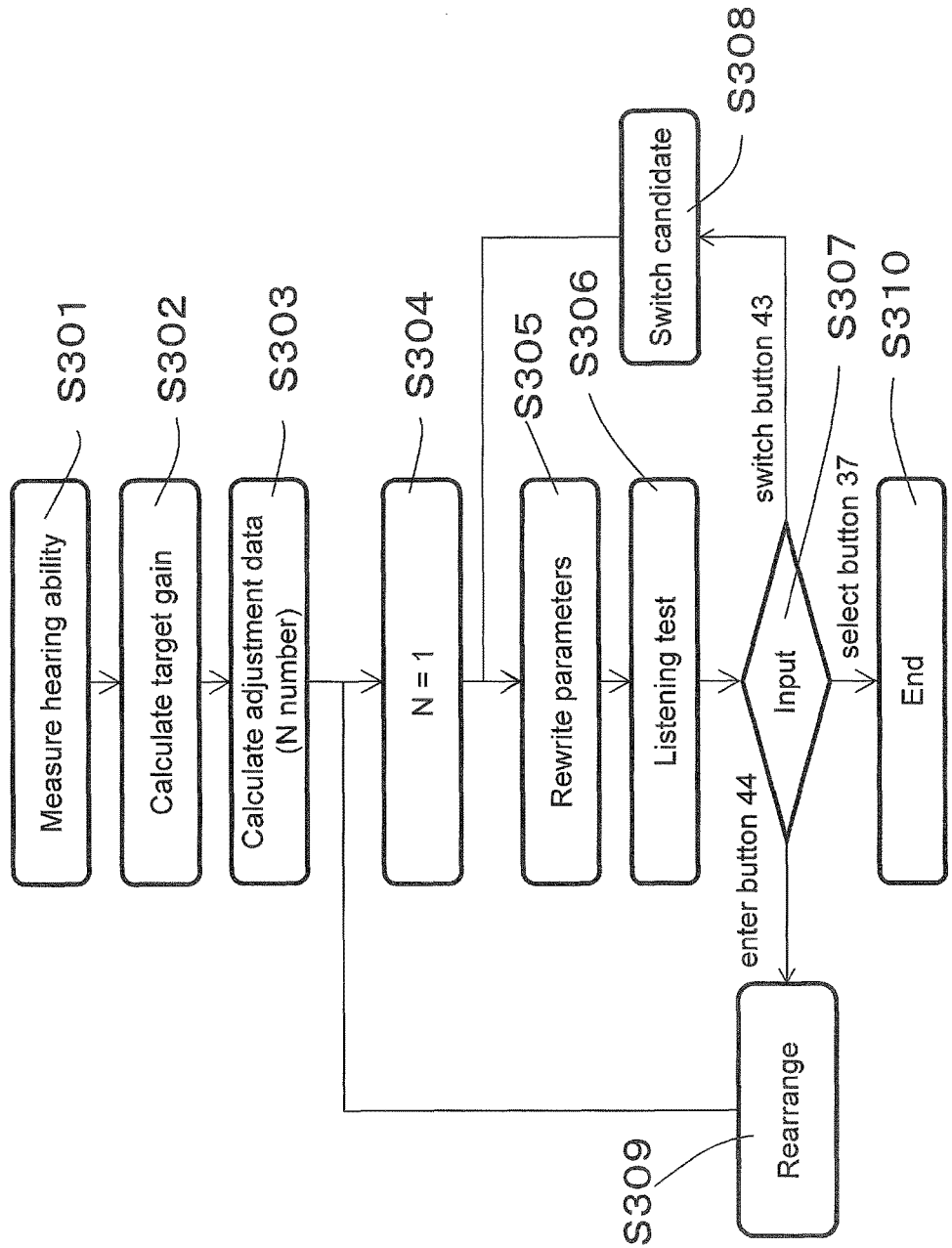
FIG. 17 is a flowchart of a hearing aid fitting method in Embodiment 3 of the present invention.

In this embodiment configured as above, the procedure shown in FIG. 17 is executed to perform fitting on the hearing aid wearer 22.

Fitting

FIG. 17 shows the flow of the hearing aid fitting method in this embodiment.

The procedure in which hearing ability data is measured for the hearing aid wearer 22, an initial fitting is performed, and then adjustment difference data is calculated (S301 to S303 in FIG. 17) is the same as in S201 to S203 in the above embodiment 2, and therefore will not be described again here.

When the adjustment difference data is calculated in the step indicated by S303 in FIG. 17, the hearing aid wearer 22 listens to evaluation sounds at various frequencies, starting with the adjustment difference data with the highest similarity to the selected adjustment difference data, and selects the best one.

Specifically, let us say that a first adjustment difference data 49 is selected (S304 in FIG. 17).

Then, the fine adjustment parameters of the first adjustment difference data 49 are read by the controller 30, and the fine adjustment parameters are rewritten (S305 in FIG. 17).

Evaluation sound data stored in the test sound database 35 is sent through the test sound output component 34 to the D/A converter 28 according to the rewritten fine adjustment parameters. After the evaluation sound data has been converted into an analog audio signal, it is outputted as an evaluation sound from the earphone 23 of the hearing aid 80, and the hearing aid wearer 22 listens to this evaluation sound (S306 in FIG. 17).

Next, the hearing aid wearer 22 presses the switch button 43 provided to the body case 25 of the hearing aid 21 to switch the adjustment difference data (S307 and S308 in FIG. 17).

Thus, the hearing aid wearer 22 successively listens to and compares evaluation sounds of the various fine adjustment parameters, starting from the first adjustment difference data 49, and presses the enter button 44 when the adjustment difference data is deemed favorable.

The sorter 47 then causes the 1 to N number of adjustment difference data (see FIG. 13) stored in the difference database 48 to be rearranged, starting from the one with the highest similarity to the adjustment difference data selected by pressing the enter button 44, on the basis of the similarity database in FIG. 16 (S307 and S309 in FIG. 17).

Figure 18:
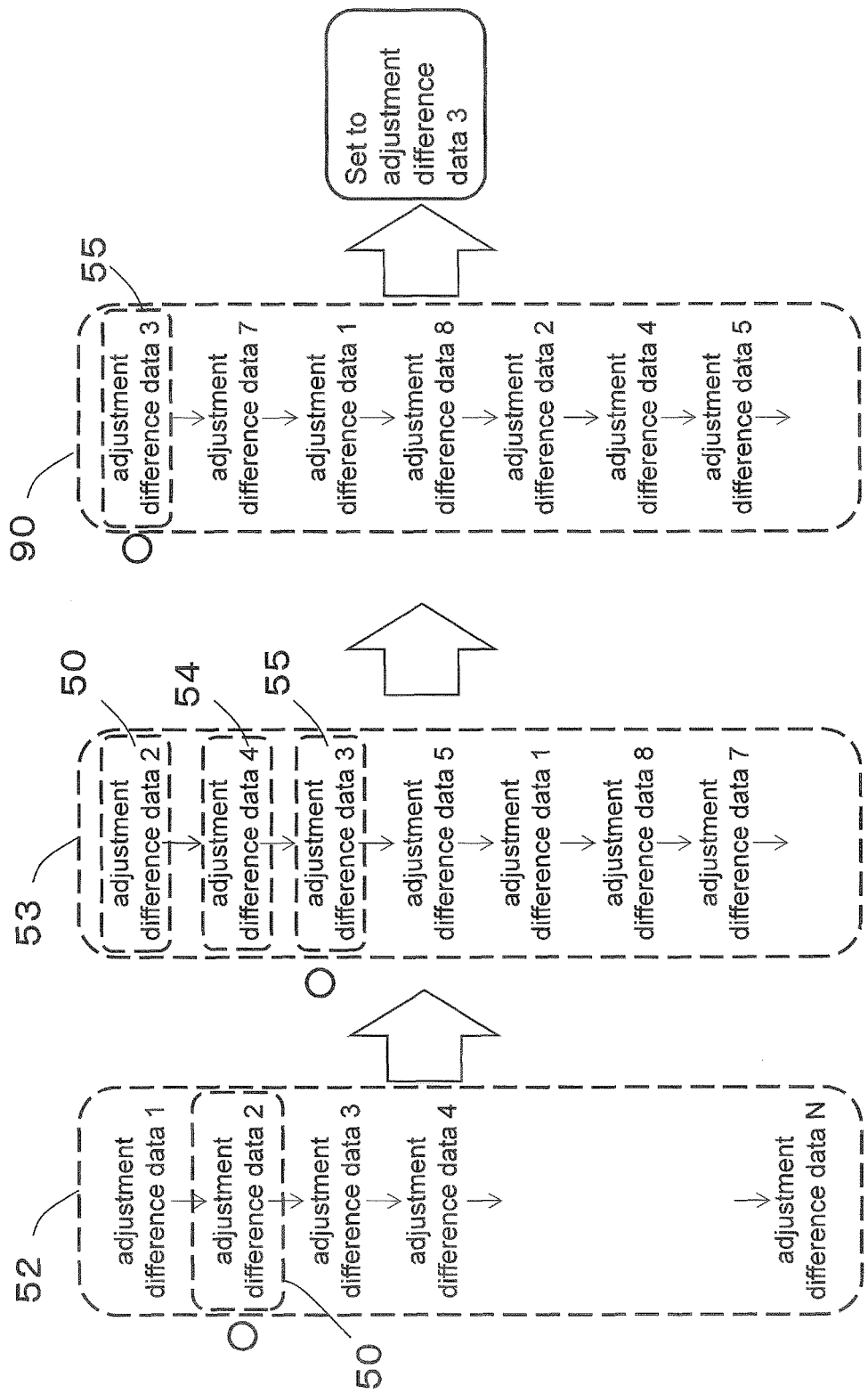
FIG. 18 is a diagram illustrating the fitting method in Embodiment 3 of the present invention.

For example, in S307, when a second adjustment difference data 50 is deemed favorable in a first sequence 52 as shown in FIG. 18, and the hearing aid wearer 22 presses the enter button 44, the sorter 47 rearranges the adjustment difference data starting from the one with the highest similarity to the second adjustment difference data 50, as in a fourth adjustment difference data 54 and a third adjustment difference data 55, in order from the second adjustment difference data 50. Specifically, the data is rearranged in order starting from the smallest value of the similarity data shown in FIG. 16. In the first sequence 52 in this example, it is unknown which adjustment difference data will be preferred, so the output was in number order, but it is also effective to present the adjustment difference data based on similarity just as in the second sequence 53 and beyond.

The procedure from S304 to S308 in FIG. 17 is repeated, and the hearing aid wearer 22 successively listens to and compares evaluation sounds adjusted on the basis of the parameters of the various adjustment difference data, in order starting from the one with the highest similarity to the selected adjustment difference data.

At this point, in the procedure of S307 and S308 in FIG. 17, every time the switch button 43 is pressed, the adjustment difference data is changed in order, starting from the one with the highest similarity to the selected adjustment difference data.

The above work is repeated until an adjustment difference data is finally determined to be the best, at which point the select button 37 is pressed to end the fitting (S310 in FIG. 17).

More specifically, to describe this using the example in FIG. 18, when the third adjustment difference data 55 is entered (an example of selection) in S307 after repeating S305 to S308 in the second sequence 53, the data is rearranged in the order of a seventh adjustment difference data (the highest similarity to the third adjustment difference data 55), the first adjustment difference data, and an eighth adjustment difference data, as indicated by a third sequence 90. Then, in this sequence, the user listens to and compares evaluation sounds adjusted according to the various sets of adjustment difference data, the third adjustment difference data 55 is deemed best in FIG. 18, and this is selected by pressing the select button 37.

Thus, the same effect can be obtained in this embodiment as in Embodiment 2 above.

Features (1)

The hearing aid 80 in this embodiment comprises the microphone 24 (an example of a receiver), the adjustment data determination component 70, the hearing aid processor 27, and the earphone 23 (an example of an output component). The microphone 24 receives audio. The adjustment data determination component 70 is connected to the database 48 (an example of a database) in which the adjustment difference data (an example of previously acquired adjustment data) obtained by the fitting of the hearing aid has been stored in a rearrangeable fashion on the basis of a specific priority order, and adjustment data for the hearing aid is determined by selecting one set of adjustment difference data from among the plurality of rearranged sets of adjustment difference data. The hearing aid processor 27 performs hearing aid processing on the received audio on the basis of the selected adjustment data. The earphone 23 outputs the audio that has undergone this hearing aid processing.

Consequently, one set of adjustment difference data can be selected from among the plurality of sets of adjustment difference data that has been rearranged on the basis of a priority order, so the adjustment difference data that best suits the user can be selected more quickly. Accordingly, fine adjustment can be carried out more efficiently.

(2)

With the hearing aid 80 in this embodiment, the adjustment data determination component 70 has the test sound output component 34 and the input component 33 (an example of a selector). The test sound output component 34 emits an evaluation-use sound on the basis of adjustment difference data designated from among a plurality of sets of rearranged fine adjustment data in order to select one set of adjustment difference data. The input component 33 selects one set of adjustment difference data on the basis of the emitted sound.

Consequently, a classification can be selected on the basis of an evaluation sound, and fitting work can be carried out more efficiently.

(3)

With the hearing aid 80 in this embodiment, a plurality of sets of adjustment difference data are rearranged on the basis of a specific priority order, using a selected adjustment difference data as a reference.

Consequently, as shown in FIG. 18, for example, a plurality of sets of adjustment difference data can be rearranged in the order of similarity to a selected previously acquired adjustment data, so the adjustment difference data that best suits the user can be selected more quickly, and fine adjustment can be carried out more efficiently.

(4)

With the hearing aid 80 in this embodiment, the priory order is determined by comparing the difference between the final adjustment data that is ultimately selected in the fitting of the hearing aid, and the initial adjustment data obtained by a specific initial adjustment method.

Consequently, the fine adjustment data can be rearranged by using a difference value that is the amount of fine adjustment from the initial adjustment data obtained in the initial fitting. Accordingly, fine adjustment work following initial fitting when the hearing aid is fitted can be carried out more efficiently.

(5)

With the hearing aid 80 in this embodiment, the specific initial adjustment method is an adjustment method that makes use of a fitting theory, and the initial adjustment data is data obtained by initial fitting using a fitting theory.

Consequently, the initial fitting can be performed using NAL-NL1 (National Acoustic Laboratories-non-linear 1), NAL-NL2, DSL (desired sensation level), i/o, DSLv5, POGO (prescription of gain/output), FIG. 6, etc., and fine adjustment can be performed more efficiently by utilizing previously acquired adjustment data rearranged on the basis of a priority order with respect to this initial fitting.

(6)

The hearing aid 80 in this embodiment further comprises the target gain calculator 32 (an example of an initial adjuster) that performs initial fitting on the basis of the hearing ability of the hearing aid user.

Consequently, initial fitting can also be performed with just the hearing aid, so there is no need to visit a retail store if the user is having trouble hearing, which is more convenient for the user.

(7)

Also, the hearing aid fitting method in this embodiment involves the use of the difference database 48 in which are stored a plurality of sets of adjustment difference data obtained by the fitting of a hearing aid, and said method comprises the steps S301 to S310 (an example of adjustment data determination steps). In S301 to S310 (an example of adjustment data determination steps), adjustment data is determined for a hearing aid by selecting one set of adjustment difference data from among the plurality of sets rearranged on the basis of a specific priority order.

Consequently, one set of adjustment difference data can be selected from among the plurality of sets of adjustment difference data that has been rearranged on the basis of a priority order, so the adjustment difference data that best suits the user can be selected more quickly. Accordingly, fine adjustment can be carried out more efficiently.

(8)

Steps S301 to S310 (an example of adjustment data determination steps) in the hearing aid fitting method in this embodiment have S305 and S306 (an example of a test sound output operation) in which an evaluation sound is outputted on the basis of fine adjustment data designated from among the plurality of sets of rearranged fine adjustment data, S307 (an example of a selection operation) in which one set of fine adjustment data is selected on the basis of the emitted evaluation sound, S309 (an example of a rearrangement operation) in which a plurality of sets of fine adjustment data are rearranged on the basis of similarity (an example of a specific priority order) using the selected fine adjustment data as a reference, and S304 to S309 (an example of a repetition operation) in which S305 and S306 (an example of a test sound output operation) and S307 (an example of a selection operation) and S308 (an example of a rearrangement operation) are repeated to determine fine adjustment data for the hearing aid.

Consequently, adjustment difference data can be selected on the basis of evaluation sounds, and fine adjustment data can be determined more efficiently.

Other Embodiments (A)

In Embodiment 2 above, a configuration was described in which the hierarchically classified database 31 was provided integrally to the hearing aid 21, but the hierarchically classified database 31 may instead be provided separately from the hearing aid 21. Also, in Embodiment 3 above, a configuration was described in which the difference database 48 was provided integrally with the hearing aid 80, but the difference database 48 may instead be provided separately from the hearing aid 80.

Figure 19:
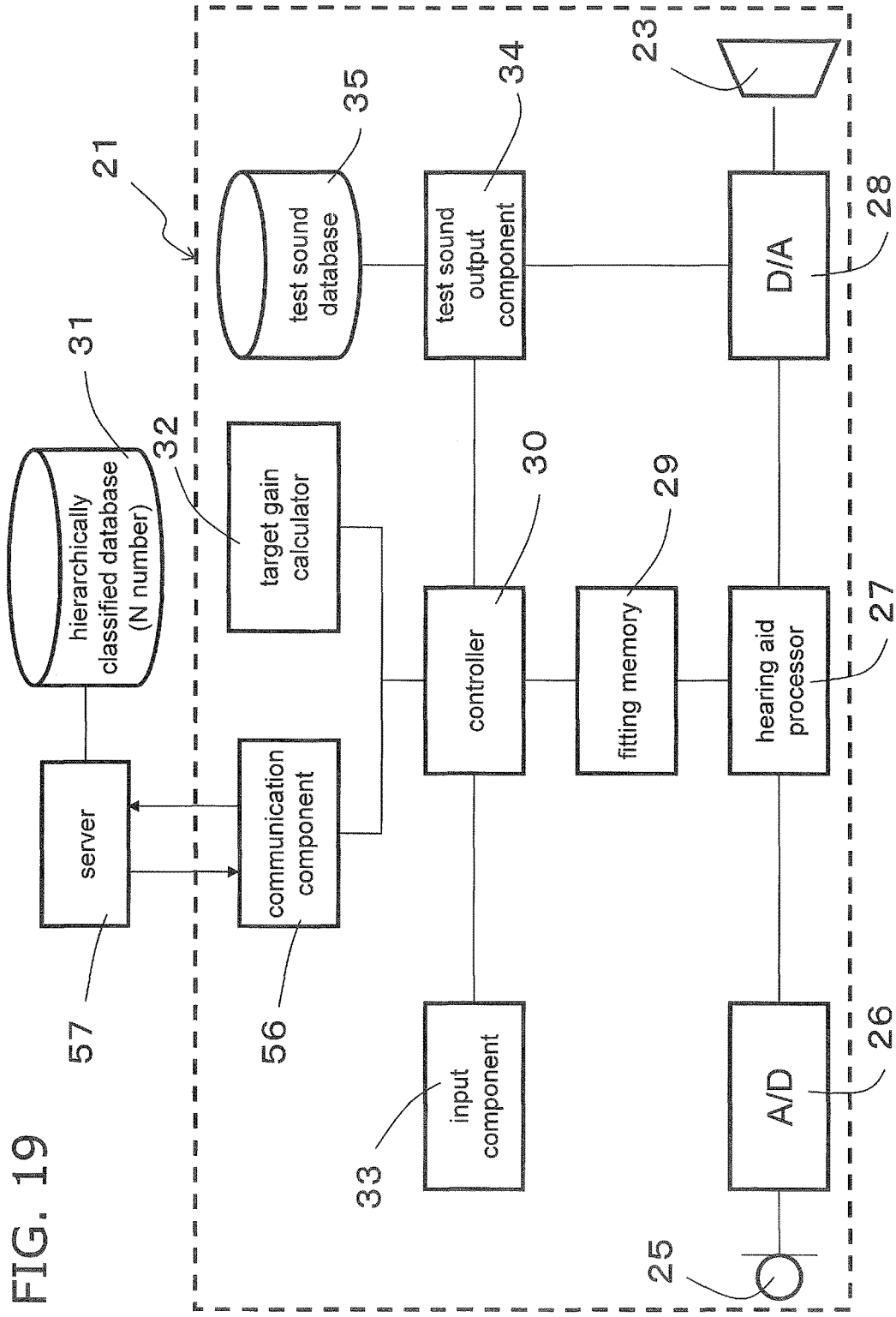
FIG. 19 is a block diagram illustrating the hearing aid fitting method in another embodiment of the present invention.

To describe this using the configuration of Embodiment 2, as shown in FIG. 19, for example, a communication component 56 may be connected to the controller 30 of the hearing aid 21, and the hierarchically classified database 31 may be connected to a server 57 that is connected by wire or wirelessly to this communication component 56, so that the hierarchically classified database 31 is connected to the controller 30 of the hearing aid 21 via the server 57 and the communication component 56.

In Embodiment 3, the difference database 48 may be connected to the server 57 as in FIG. 18. Also, the sorter 47 may be provided to the server 57, rather than being provided on the hearing aid 80 side.

(B)

With the hearing aid 21 in Embodiments 2 and 3 above, if an option can be selected, such as the ear tip mounted to the earphone 23 of the hearing aid 21, the data stored in the hierarchically classified database 31 in Embodiment 2 above or in the difference database 48 in Embodiment 3 above may be such that a database corresponding to this option can be selected.

Specifically, as shown in FIG. 10, the option select button 59 may be provided to the body case 25 of the hearing aid 21, so that a database corresponding to an option such as the ear tip being used, for example, can be selected.

(C)

A program, for example, may be used for all or part of the hearing aid fitting method in Embodiments 1 to 3 above.

For instance, a program may be used for all or part of the operation of steps S100 to S107 (an example of adjustment data determination steps) in which adjustment data is determined for a hearing aid by selecting a classification out of a plurality of clusters in each hierarchical level in the fitting method of Embodiment 1.

Also, a program may be used for all or part of the operation of steps S201 to S211 (an example of adjustment data determination steps) in which adjustment data is determined for a hearing aid by selecting one set of the adjustment different data from among the plurality of sets of the adjustment different data in each hierarchical level in the fitting method of Embodiment 2.

Also, a program may be used for all or part of the operation of steps S301 to S310 (an example of adjustment data determination steps) in which adjustment data is determined for a hearing aid by selecting one set of previously acquired adjustment data from among the plurality of sets of previously acquired adjustment data rearranged according to a specific priority order in the fitting method of Embodiment 3.

All or part of the operation, steps, etc., of the control method in Embodiments 1 to 3 above may be carried out by a central processing unit (CPU) in a computer. The above-mentioned program operates in conjunction with the computer.

Also, as a utilization mode for the above-mentioned program, for example, data may be recorded to a ROM or other such recording medium that can be read by a computer. Furthermore, the program utilization mode may be one in which data is transmitted through light, radio waves, or another such transmission medium, or through a transmission medium such as the Internet, and then read by a computer. For example, the fitting device 1 or the hearing aid 21 or 80 in the above embodiments may be connected by USB or the like to a computer, and a program that carries out the above-mentioned fitting method may be transmitted over the Internet. This computer is not limited to hardware such as a CPU, and may instead be firmware or an OS. Also, all or part of the steps, processing, etc., in the adjustment data determination step may be realized by hardware, or by software. Or, it may be realized by a mixture of software and hardware.

INDUSTRIAL APPLICABILITY

The hearing aid fitting device, hearing aid, and hearing aid fitting method of the present invention reduce the work entailed by a fitting, and allow the fitting to be carried out more efficiently, in less time, and are therefore expected to find wide application in the fitting of hearing aids.

REFERENCE SIGNS LIST 1 fitting device
2 display component
3 keyboard
4 mouse
5 connector box
6 hearing aid
7 user
8 controller
9 connector
10 memory
11 candidate setting component
12 hierarchically classified database
19 selector
20 adjustment data determination component
21 hearing aid
22 hearing aid wearer
23 earphone
24 microphone
25 body case
26 A/D converter
27 hearing aid processor
28 D/A converter
29 fitting memory
30 controller
31 hierarchically classified database
32 target gain calculator
33 input component
34 test sound output component
35 test sound database
36 adjustment start button
37 select button
38 column
39 heading
40 first hierarchical level
41 first classification
42 second classification
43 switch button
44 enter button
45 second hierarchical level
46 third hierarchical level
47 sorter
48 difference database
49 first adjustment difference data
50 second adjustment difference data
51 region
52 first sequence
53 second sequence
54 fourth adjustment difference data
55 third adjustment difference data
56 communication component
57 server
61 $1\text{-}1^{th}$ classification
62 $1\text{-}2^{th}$ classification
63 $2\text{-}1^{th}$ classification
64 $2\text{-}2^{th}$ classification
65 $1\text{-}1\text{-}1^{th}$ classification
66 $1\text{-}1\text{-}2^{th}$ classification
70 adjustment data determination component
80 hearing aid
90 third sequence

The invention claimed is:

1. A hearing aid fitting device, comprising:
a database in which a plurality of sets of previously acquired adjustment data obtained by a hearing aid fitting are stored after being classified into a plurality of hierarchical layers of clusters according to the similarity in amount of adjustment, wherein each cluster includes at least one of the sets of previously acquired adjustment data, the clusters of a relatively lower hierarchical layer are within a cluster of a relatively next-higher hierarchical layer, and each cluster at each hierarchical layer has a previously acquired data set that is the representative adjustment data of the cluster; and
an adjustment data determination controller that determines adjustment data for a hearing aid by selecting a cluster from among the clusters in each hierarchical layer based on a test sound produced using the representative adjustment data in each cluster.

2. The hearing aid fitting device according to claim 1, wherein the amount of adjustment is a difference between final adjustment data that is ultimately determined in the hearing aid fitting, and initial adjustment data obtained by a specific initial adjustment method.

3. The hearing aid fitting device according to claim 1, further comprising a transmitter that transmits to the hearing aid representative adjustment data,
wherein the adjustment data determination controller has a selector that selects one of the clusters in each hierarchical layer according to evaluation-use audio emitted from the hearing aid that has been adjusted on the basis of the representative adjustment data.

4. The hearing aid fitting device according to claim 3, wherein the representative adjustment data is an average of all the previously acquired adjustment data included in the cluster, or previously acquired adjustment data that is the most similar to the average.

5. The hearing aid fitting device according to claim 3, wherein a plurality of sets of the previously acquired adjustment data are assigned a priority order among the clusters, and the representative adjustment data is previously acquired adjustment data that is the highest in the priority order.

6. The hearing aid fitting device according to claim 5, wherein the priority order is the order of frequency of use in the hearing aid fitting.

7. The hearing aid fitting device according to claim 1, wherein the adjustment data determination controller further has a display that displays information related to the cluster in each of the hierarchical layers in order to select the cluster.

8. A hearing aid, comprising:
a receiver that receives audio;
an adjustment data determination controller that is connected to a database in which previously acquired adjustment data obtained by a hearing aid fitting is stored after being classified into a plurality of hierarchical layers of clusters according to similarity in amount of adjustment, wherein each cluster includes at least one of the sets of previously acquired adjustment data, the clusters of a relatively lower hierarchical layer are within a cluster of a relatively next-higher hierarchical layer, and each cluster at each hierarchical layer has a previously acquired data set that is the representative adjustment data of the cluster, and that determines adjustment data for a hearing aid by selecting a cluster from among the clusters in each hierarchical layer based on a test sound produced using the representative adjustment data in each cluster;
a hearing aid processor that performs hearing aid processing on the received audio, on the basis of the adjustment data thus determined; and
an output that outputs the audio that has undergone the hearing aid processing.

9. The hearing aid according to claim 8, wherein the amount of adjustment is a difference between final adjustment data that is ultimately determined in the fitting of the hearing aid, and initial adjustment data obtained by a specific initial adjustment method.

10. The hearing aid according to claim 9, wherein the specific initial adjustment method is an adjustment method featuring a fitting theory, and
the initial adjustment data is data obtained by an initial fitting in which a fitting theory is used.

11. The hearing aid according to claim 10, further comprising an initial adjuster for performing the initial fitting on the basis of a hearing ability of a hearing aid user.

12. The hearing aid according to claim 8,
wherein the adjustment data determination component has:
a test sound output component that emits the test sound on the basis of the representative adjustment data that represents the clusters; and
a selector that selects one of the clusters based on the emitted sound.

13. The hearing aid according to claim 8,
wherein the plurality of sets of previously acquired adjustment data are assigned a priority order among the classifications, and
representative adjustment data, which represents the cluster, is data that is the highest in the priority order.

14. The hearing aid according to claim 8, wherein the database is connected by communication with the adjustment data determination component.

15. A hearing aid fitting method that makes use of a database in which a plurality of sets of previously acquired adjustment data obtained by a hearing aid fitting are stored after being classified into a plurality of hierarchical layers of clusters according to similarity in amount of adjustment, wherein each cluster includes at least one of the sets of previously acquired adjustment data, the clusters of a relatively lower hierarchical layer are within a cluster of a relatively next-higher hierarchical layer, and each cluster at each hierarchical layer has a previously acquired data set that is the representative adjustment data of the cluster,
said method comprising determining adjustment data for a hearing aid by selecting a cluster from among the clusters in each hierarchical layer based on a test sound produced using the representative adjustment data in each cluster.

16. The hearing aid fitting method according to claim 15, further comprising:
a test sound output operation in which adjustment is performed on the hearing aid on the basis of representative adjustment data that represents the classification for each of the plurality of clusters in each hierarchical layer, and the test sound is outputted from the adjusted hearing aid;
a selection operation in which one of the clusters is selected from among the clusters in each hierarchical level, on the basis of the test sound; and
a repetition operation in which the test sound output operation and the selection operation are repeated to determine the adjustment data for the hearing aid.

17. The hearing aid fitting method according to claim 16, wherein the representative adjustment data is an average of all the previously acquired adjustment data included in the cluster, or previously acquired adjustment data that is the most similar to the average.

18. The hearing aid fitting method according to claim 16, wherein the representative adjustment data is the previously acquired adjustment data used most often in the fitting of a hearing aid.

19. The hearing aid fitting method according to claim 16, further comprising a display operation in which information related to clusters is displayed for each hierarchical layer,
wherein the test sound output operation is performed by selecting information related to the displayed classifications.

20. A non-transitory computer readable medium comprising:
a program that causes a computer to execute determining in a hearing aid fitting method that makes use of a database in which a plurality of sets of previously acquired adjustment data obtained by a hearing aid fitting are stored after being classified into a plurality of hierarchical layers of clusters according to similarity in amount of adjustment, wherein each cluster includes at least one of the sets of previously acquired adjustment data, the clusters of a relatively lower hierarchical layer are within a cluster of a relatively next-higher hierarchical layer, and each cluster at each hierarchical layer has a previously acquired data set that is the representative adjustment data of the cluster, in which adjustment data is determined for a hearing aid by selecting the cluster from among the clusters in each hierarchical layer based on a test sound produced using the representative adjustment data in each cluster.

* * * * *